(12) United States Patent
Nixon et al.

(10) Patent No.: US 9,255,927 B2
(45) Date of Patent: Feb. 9, 2016

(54) METHODS OF DEVELOPING A PROGNOSIS FOR PANCREATIC CANCER AND PREDICTING RESPONSIVENESS TO CANCER THERAPEUTICS

(75) Inventors: Andrew B. Nixon, Durham, NC (US); Herbert I. Hurwitz, Durham, NC (US); Herbert Pang, Durham, NC (US); Mark D. Starr, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 0 days.

(21) Appl. No.: 14/115,825

(22) PCT Filed: May 7, 2012

(86) PCT No.: PCT/US2012/036779
§ 371 (c)(1),
(2), (4) Date: Jan. 15, 2014

(87) PCT Pub. No.: WO2012/151574
PCT Pub. Date: Nov. 8, 2012

(65) Prior Publication Data
US 2014/0127193 A1 May 8, 2014

Related U.S. Application Data

(60) Provisional application No. 61/482,757, filed on May 5, 2011.

(51) Int. Cl.
| G01N 33/574 | (2006.01) |
| G01N 33/74 | (2006.01) |
| A61K 39/395 | (2006.01) |
| C12Q 1/68 | (2006.01) |
| C07K 16/22 | (2006.01) |
| A61K 31/7068 | (2006.01) |
| A61K 39/00 | (2006.01) |

(52) U.S. Cl.
CPC ...... *G01N 33/57438* (2013.01); *A61K 31/7068* (2013.01); *A61K 39/39558* (2013.01); *C07K 16/22* (2013.01); *A61K 2039/505* (2013.01)

(58) Field of Classification Search
CPC ............ G01N 2800/52; G01N 2333/515; G01N 33/57419; G01N 2800/60; G01N 33/57438; G01N 33/74; G01N 33/57484; A61K 39/395; A61K 31/00; C12Q 1/6886; C12Q 2600/106
See application file for complete search history.

(56) References Cited

U.S. PATENT DOCUMENTS

| 2006/0223770 A1 | 10/2006 | Fougerolles et al. |
| 2010/0055099 A1 | 3/2010 | Filvaroff et al. |
| 2011/0076271 A1 | 3/2011 | Schmidt et al. |
| 2011/0257035 A1* | 10/2011 | Pena ................................ 506/9 |
| 2012/0142012 A1* | 6/2012 | Hacker et al. ................ 435/6.12 |

FOREIGN PATENT DOCUMENTS

WO 2009/155504 12/2009

OTHER PUBLICATIONS

Goede et al., Br J Cancer. Oct. 26, 2010; 103(9): 1407-1414.*
George, et al., "VEGF-A, VEGF-C, VEGF-D in colorectal cancer progression," Neoplasia (2001) 3(5):420-427.
Kopetz, S. et al., "Phase II trial of infusional fluorouracil, irinotecan, and bevacizumab for metastatic colorectal cancer: efficacy and circulating angiogenic biomarkers associated with therapeutic resistance," J Clin Oncol (2010) 28:453-9.
Lieu, C.H., et al., "Relative impact of chemotherapy with or without bevacizumab on cytokines and angiogenic factors (CAFs) in metastatic colorectal cancer," J Clin Oncol (2011) 29:(suppl 4; Abstract 401) (Abstract).
Lieu, C.H., et al., "The association of alternate VEGF ligands with resistance to anti-VEGF therapy in metastatic colorectal cancer," PLoS One (2013) 8(10): p. e77117.
Liu, Y., et al., "Correlation of angiogenic biomarker signatures with clinical outcomes in metastatic colorectal cancer patients receiving capecitabine, oxaliplatin, and bevacizumab," Cancer Med. (2013) 2(2):234-42.
Martin, et al., "High-sensitivity array analysis of gene expression for the early detection of disseminated breast tumor cells in peripheral blood," PNAS (2001) 98(5):2646-2651.
Nixon, A..B., et al., "Prognostic and predictive blood-based biomarkers in patients with advanced pancreatic cancer: Results from CALGB80303 (Alliance)," Clin Cancer Res. (2013) 19(24):6957-66.
Weickhardt A.J. et al., "Vascular endothelial growth factors (VEGF) and VEGF receptor expression as predictive biomarkers for benefit with bevacizumab in metastatic colorectal cancer (mCRC): Analysis of the phase III MAX study," J Clin Oncol. (2011) 29:3531 (suppl; Abstract).
International Search Report and Written Opinion dated Sep. 19, 2012 in International Patent Application No. PCT/US2012/036779 (18 pages).
International Preliminary Report on Patentability dated Nov. 14, 2013 in International Patent Application No. PCT/US2012/036779 (12 pages).

* cited by examiner

*Primary Examiner* — Daniel C Gamett
(74) *Attorney, Agent, or Firm* — Andrus Intellectual Property Law, LLP

(57) ABSTRACT

Methods of predicting responsiveness of a cancer in a subject to a cancer therapy including a VEGF targeting agent are provided herein. The methods include detecting the expression level of at least one biomarker selected from ANG-2, SDF-1 and VEGF-D in a sample from the subject and using the expression levels to determine whether the VEGF targeting agent will be effective to treat the cancer in the subject. The predictions may be used to develop treatment plans for the subjects. Methods of developing a prognosis for a subject with pancreatic cancer are also provided. These methods include determining the expression level of IGFBP-1, PDGF-AA and at least one of IL-6 or CRP in a sample from a subject with pancreatic cancer.

6 Claims, 5 Drawing Sheets

A.

B.

METHODS OF DEVELOPING A PROGNOSIS FOR PANCREATIC CANCER AND PREDICTING RESPONSIVENESS TO CANCER THERAPEUTICS

CROSS-REFERENCE TO RELATED APPLICATIONS

This patent application is a national stage filing under 35 U.S.C. 371 of International Application No. PCT/US2012/036779, filed May 7, 2012, which claims the benefit of priority of U.S. Provisional Patent Application No. 61/482,757, filed May 5, 2011, both of which are incorporated herein by reference in their entirety.

INTRODUCTION

The goal of all targeted therapies and personalized medicine in general is to define which patients are most or least likely to benefit or have toxicity from a given treatment and to provide patients with a more accurate prognosis. Similarly, almost all cancer patients develop resistance to any given therapy; defining the mechanisms of this resistance helps direct the use of other therapies, including combination regimens to delay, prevent, or overcome this resistance.

Clinically, there have been several reports of biomarkers whose expression levels change in response to treatment. Multiple groups have shown that increased levels of various angiogenesis factors, including VEGF, correlate with worse prognosis or outcome in general. Similarly, several groups have described in patients changes in various angiogenesis factors with anti-VEGF treatment, including VEGF, PIGF, SDF1, Ang2, and sVEGFR2, among others. Many of these changes are seen in preclinical models, even in non-tumor bearing mice suggesting these responses are at least partially host derived. In preclinical models, factors mediating resistance to anti-VEGF therapy have been described. In the clinic, however, markers that predict which patients will derive greater or lesser benefit from anti-VEGF therapy have been elusive. This may relate to many factors, including technical limitations in assay methods and target abundance or stability. The difficulty in identifying such biomarkers may also relate to the context and complexity of co- and counter-regulation of angiogenesis. Lastly, this information can only be reliably derived from large randomized trials.

By way of example, pancreatic cancer is one of the leading causes of cancer related death worldwide. Despite modest benefits associated with currently available treatments, the median survival for patients with metastatic pancreatic adenocarcinoma remains under 1 year (6-9 months). The clinical hallmarks of pancreatic cancer include marked desmoplasia, early metastases, cachexia, and hypercoaguability. The pathophysiology underlying these conditions has been associated with multiple factors associated with tumor angiogenesis and inflammation. While many angiogenic and inflammatory makers have been profiled in pancreatic cancer, these analyses have typically been limited by the size and quality of the available datasets, and by the technical limitations of standard assay ELISA methods, which significantly limited the number of factors that could be evaluated in a given sample. Having biomarkers or sets of biomarkers that can provide pancreatic cancer patients with a more accurate prognosis and predictions regarding the responsiveness to cancer therapies would be helpful to patients and to society.

SUMMARY

Provided herein are methods of predicting responsiveness of a cancer in a subject to a cancer therapy including a VEGF targeting agent, methods of developing a prognosis for a subject diagnosed with pancreatic cancer, and methods of developing treatment plans for subjects with cancer.

In one aspect, methods of predicting responsiveness of a cancer in a subject to a cancer therapy including a VEGF targeting agent are provided. These methods include determining the expression level of at least one biomarker selected from Ang-2, SDF-1 and VEGF-D in a sample from the subject. The levels of the biomarkers are then compared to a reference level of the biomarker and the comparison is used to predict the responsiveness of the cancer to treatment with the cancer therapy including a VEGF targeting agent. In one embodiment, if the levels of VEGF-D are determined to be low (i.e. less than 1050 pg/mL), then treatment with a cancer therapy including a VEGF targeting agent is predicted to be beneficial. In another embodiment, if the levels of VEGF-D are determined to be in the mid-to high range (i.e. more than 1100 pg/mL), then treatment with a cancer therapy including a VEGF targeting agent is not predicted to be beneficial. In another embodiment, if the levels of ANG-2 and SDF-1 are low (i.e. 305 pg/mL and 1100 pg/mL, respectively), then treatment with a cancer therapy including a VEGF targeting agent is not predicted to be beneficial. In another embodiment, if the levels of SDF-1 are high (i.e. more than 1100 pg/mL) and the levels of OPN are low (i.e. less than 75 ng/mL), then treatment with a cancer therapy including a VEGF targeting agent is predicted to be beneficial.

In another aspect, methods of developing treatment plans for subjects with cancer are provided. In these methods the prediction of the responsiveness of the cancer to treatment with a cancer therapy including a VEGF targeting agent is used to select a cancer therapy including a VEGF targeting agent if the cancer is predicted to respond to an anti-VEGF therapy. In an alternative embodiment, a prediction suggesting that a VEGF targeting agent will not be effective or will be counter-productive will result in development of a treatment plan excluding a VEGF targeting agent.

In yet another aspect, methods of developing a prognosis for a subject diagnosed with pancreatic cancer are provided. These methods include determining an expression level of IGFBP-1, PDGF-AA and at least one of IL-6 and CRP in a sample from the subject. The levels of the biomarkers are then compared to reference levels. Finally the comparison is used to determine a survival prognosis for the subject. In one embodiment, if the levels of IGFBP-1, PDGF-AA and IL-6 are low (i.e. less than 13,500 pg/mL, 250 pg/mL and 20 pg/mL, respectively), then the survival prognosis is more than 6 months. In this embodiment, if the levels of PDGF-BB and TSP-2 are also determined to be low (i.e. less than 190 pg/mL and 21,000 pg/mL, respectively) then the survival prognosis is more than 6 months. In another embodiment, if the levels of IGFBP-1, PDGF-AA and CRP are low (i.e. less than 13,500 pg/mL, 250 pg/mL and 21,000 ng/mL, respectively), then the survival prognosis is more than 6 months. In this embodiment, if the levels of PAI-1 total and PEDF are also determined to be low (i.e. less than 28,000 pg/mL and 3,600 ng/mL, respectively) then the survival prognosis is more than 6 months.

DETAILED DESCRIPTION

Figure 1:
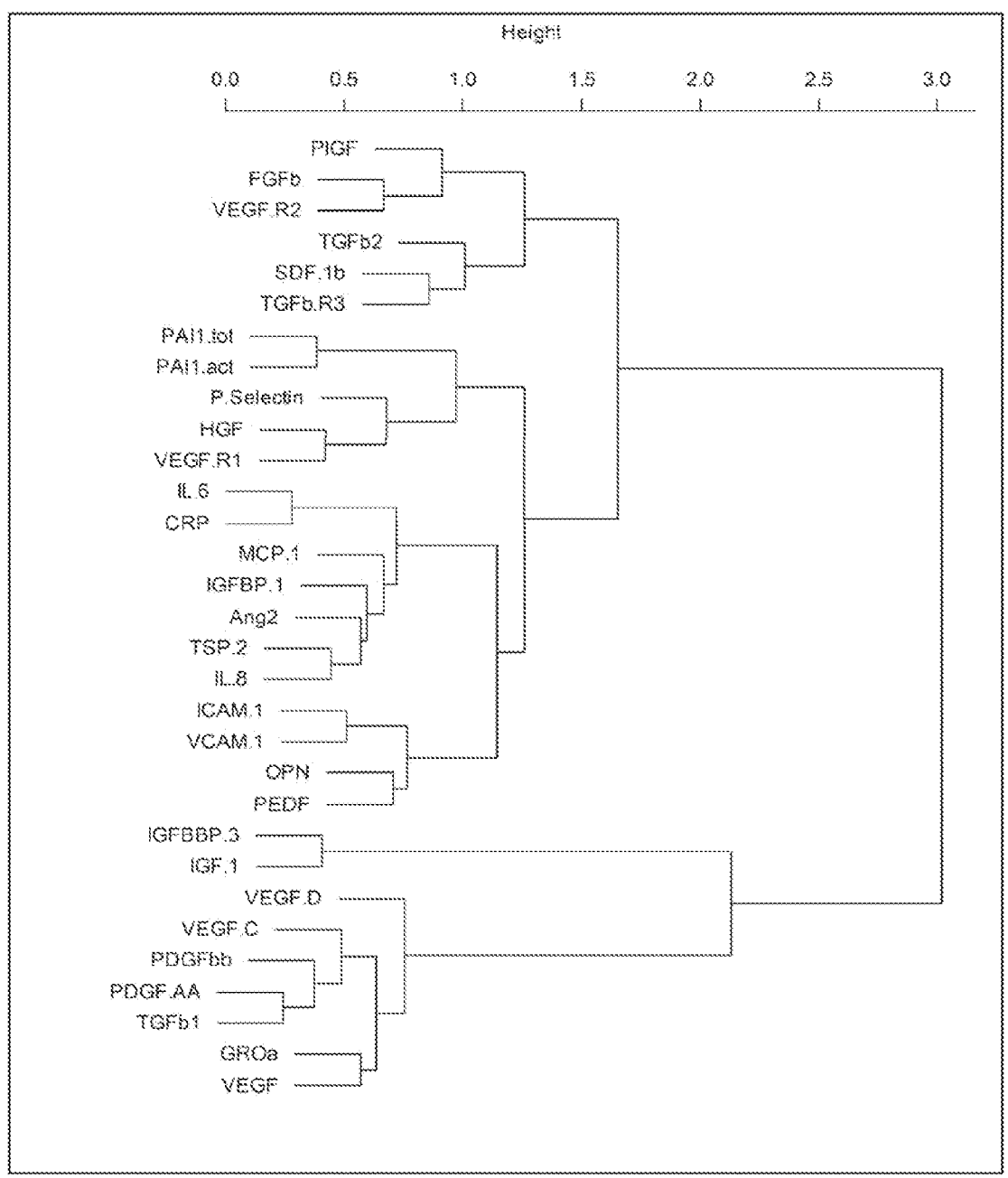
FIG. 1 is a Spearman-based dendrogram showing the relatedness of the biomarkers analyzed in the Examples.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure, as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

Unless otherwise defined, all technical terms used herein have the same meaning as commonly understood by one of ordinary skill in the art to which this disclosure belongs.

We sought to identify which growth factors, cytokines, or other blood-based markers predict for sensitivity or resistance to a given therapy, particularly anti-VEGF therapy. In this case, we were particularly interested in determining which factors (or groups of factors) predict for sensitivity and acquired resistance to bevacizumab, and/or which factors predict for bevacizumab related toxicity. Describing patterns of co- and counter-regulation among these factors was thought to be critical to understanding this sensitivity and resistance.

Methods of predicting responsiveness of a cancer in a subject to a cancer therapy including a VEGF targeting agent, methods of developing a prognosis for a subject diagnosed with pancreatic cancer, and methods of developing treatment plans for subjects with cancer are provided herein. The methods all rely on detecting or determining the expression level of at least one biomarker or combinations of biomarkers in a sample from a subject diagnosed with cancer. Suitably, the cancer is a solid tumor.

Thus, the present methods permit the personalization of therapy amongst cancer patients, wherein a subject's biomarker profile is predictive of, or indicative of, treatment efficacy and or survival. The methods disclosed herein can be used in combination with assessment of conventional clinical, factors, such as tumor size, tumor grade, lymph node status, family history, and analysis of expression level of additional biomarkers. In this manner, the methods of the present disclosure permit a more accurate evaluation of prognosis and cancer therapy effectiveness.

In one embodiment, the method includes determining the expression levels of the proteins or the RNA transcripts for the biomarkers provided herein in Tables 5-13 in a sample from a patient with cancer. Biomarker expression in some instances may be normalized against the expression levels of all proteins or RNA transcripts in the sample, or against a reference set of proteins or RNA transcripts in the sample. The level of expression of the biomarkers is indicative of the prognosis for the subject or predictive of the effectiveness of a particular treatment.

The methods of the present disclosure can also be used to assist in selecting appropriate courses of treatment and to identify patients that would benefit from a particular course of therapy. Thus, the expression of the particular biomarkers described herein provides insight into which cancer treatment regimens will be most effective for the patient. This information can be used to generate treatment plans for the patient to prolong survival and minimize side effects or cancer therapy related toxicity.

In some embodiments described herein, prognostic performance of the biomarkers and/or other clinical parameters was assessed utilizing a Cox Proportional Hazards Model Analysis, which is a regression method for survival data that provides an estimate of the hazard ratio and its confidence interval. The Cox model is a well-recognized statistical technique for exploring the relationship between the survival of a patient and particular variables. This statistical method permits estimation of the hazard risk) of individuals given their prognostic variables (e.g., expression level of particular biomarkers, as described herein). Survival data are commonly presented as Kaplan-Meier curves or plots. The "hazard ratio" is the risk of death at any given time point for patients displaying particular prognostic variables. See generally Spruance et al., Antimicrob. Agents &. Chemo. 48:2787-92, 2004. Methods for assessing statistical significance are well known in the art and include, for example, using a log-rank test, Cox proportional hazards model and Kaplan-Meier curves. In some aspects of the invention, a p-value of less than 0.05 constitutes statistical significance.

As used herein, the term "subject" and "patient" are used interchangeably and refer to both human and nonhuman animals. The term "non-human animals" of the disclosure includes all vertebrates, e.g., mammals and non-mammals, such as nonhuman primates, sheep, dog, cat, horse, cow, chickens, amphibians, reptiles, and the like. Preferably, the subject is a human patient. More preferably, the subject is a human patient diagnosed with cancer or undergoing, or about to undergo, a cancer treatment regimen.

The biomarkers of the present disclosure include proteins and genes encoding the proteins. The biomarkers analyzed are provided in Table 1 along with an indication of the commonly used abbreviations for each marker. Such biomarkers include DNA comprising the entire or partial sequence of the nucleic acid sequence encoding the biomarker, or the complement of such a sequence. The biomarker nucleic acids also include RNA comprising the entire or partial sequence of the nucleic acid sequences encoding the proteins of interest. A biomarker protein comprises the entire or partial amino acid sequence of any of the biomarker proteins or polypeptides.

TABLE 1

| Angiogenic Factors analyzed | | | | |
|---|---|---|---|---|
| Soluble Angiogenic Factors | Matrix-Derived Angiogenic Factors | Markers of Coagulation | Markers of Vascular Activation and Inflammation | |
| ANG-2 | PEDF | Osteopontin | CRP | Gro-a |
| bFGF | PlGF | TGFb1 | PAI-1 Active | ICAM-1 |
| HGF | VEGF-A | TGFb2 | PAI-1 Total | IL-6 |
| IGFBP1 | VEGF-C | TSP2 | | IL-8 |

TABLE 1-continued

Angiogenic Factors analyzed

| Soluble Angiogenic Factors | Matrix-Derived Angiogenic Factors | Markers of Coagulation | Markers of Vascular Activation and Inflammation |
|---|---|---|---|
| IGFBP3 | VEGF-D | | MCP-1 |
| PDGF-AA | sVEGFR1 | | P-selectin |
| PDGF-BB | sVEGFR2 | | SDF-1 |
| | | | VCAM-1 |

Abbreviations:
ANG-2, angiopoietin-2;
bFGF, basic fibroblast growth factor;
HGF, hepatocyte growth factor;
IGFBP, insulin-like growth factor-binding protein;
PDGF, platelet-derived growth factor;
PEDF, pigment epithelium-derived factor,
PlGF, placental growth factor;
VEGF, vascular endothelial growth factor;
sVEGFR, soluble vascular endothelial growth factor receptor;
TGFβ, transforming growth factor beta;
TSP, thrombospondin;
CRP, c-reactive protein;
PAI-1, plasminogen activator inhibitor-1;
Gro-α; growth regulated oncogene-alpha;
ICAM-1, intercellular adhesion molecule 1;
IL, interleukin;
MCP-1, macrophage chemoattractant protein-1;
SDF-1 stromal cell-derived factor-1;
VCAM-1, vascular cell adhesion molecule 1.

Fragments and variants of biomarker genes and proteins are also encompassed by the present invention. By "fragment" is intended a portion of the polynucleotide or a portion of the amino acid sequence and hence protein encoded thereby. Polynucleotides that are fragments of a biomarker nucleotide sequence generally comprise at least 10, 15, 20, 50, 75, 100, 150, 200, 250, 300, 350, 400, 450, 500, 550, 600, 650, 700, 800, 900, 1,000, 1,200, or 1,500 contiguous nucleotides, or up to the number of nucleotides present in a full-length biomarker polynucleotide disclosed herein. A fragment of a biomarker polynucleotide will generally encode at least 15, 25, 30, 50, 100, 150, 200, or 250 contiguous amino acids, or up to the total number of amino acids present in a full-length biomarker protein of the invention. "Variant" is intended to mean substantially similar sequences. Generally, variants of a particular biomarker of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that biomarker as determined by sequence alignment programs.

A "biomarker" is a gene or protein whose level of expression in a sample is altered compared to that of a normal or healthy sample or is indicative of a condition. The biomarkers disclosed herein are genes and proteins whose expression level correlates with cancer, particularly pancreatic cancer, prognosis or responsiveness of the cancer to a cancer therapy including a VEGF targeting agent.

In particular embodiments, the methods for predicting or prognosticating a cancer therapy in a subject includes collecting a patient body sample. The sample may or may not include cells. In particular, the methods described herein may be performed without requiring a tissue sample or biopsy and need not contain any cancer cells. In the Examples, plasma was used. "Sample" is intended to include any sampling of cells, tissues, or bodily fluids in which expression of a biomarker can be detected. Examples of such samples include, but are not limited to, biopsies, smears, blood, lymph, urine, saliva, or any other bodily secretion or derivative thereof. Blood can include whole blood, plasma (citrate, EDTA, heparin), serum, or any derivative of blood. Samples may be obtained from a patient by a variety of techniques available to those skilled in the art. Methods for collecting various samples are well known in the art.

Any methods available in the art for detecting expression of biomarkers are encompassed herein. The expression of a biomarker of the invention can be detected on a nucleic acid level (e.g., as an RNA transcript) or a protein level. By "detecting or determining expression" is intended determining the quantity or presence of a protein or its RNA transcript for at least one of the biomarkers of Table 1. Thus, "detecting expression" encompasses instances where a biomarker is determined not to be expressed, not to be detectably expressed, expressed at a low level, expressed at a normal level, or overexpressed.

Methods suitable for detecting or determining the expression levels of biomarkers are known to those of skill in the art and include, but are not limited to, ELISA, immunofluorescence, FACS analysis, Western blot, magnetic immunoassays, and both antibody-based microarrays and non-antibody-based microarrays. In the past, the gold standard for detection of growth factors and cytokines in blood was the use of ELISAs; however, multiplex technology offers an attractive alternative approach for cytokine and growth factor analysis. The advantages of multiplex technology compared to traditional ELISA assays are conservation of patient sample, increased sensitivity, and significant savings in cost, time and labor.

Several multiplex platforms currently exist. The Luminex bead-based systems are the most established, being used to detect circulating cytokines and growth factors in both mice and humans. This method is based on the use of microparticles that have been pre-coated with specific antibodies. These particles are then mixed with sample and the captured analytes are detected using specific secondary antibodies. This allows for up to 100 different analytes to be measured simultaneously in a single microplate well. The advantages of this flow cytometry-based method compared to traditional ELISA assays are in the conservation of patient samples as well as significant savings in terms of cost and labor. An alternative, plate-based system is produced by Meso Scale Discovery (MSD). This system utilizes its proprietary Multi-Array® and Multi-Spot® microplates with electrodes directly integrated into the plates. This enables the MSD system to have ultra-sensitive detection limits, high specificity, and low background signal. Another plate-based multiplex system is the SearchLight Plus CCD Imaging System produced by Aushon Biosystems. This novel multiplexing technology allows for the measurement of up to 16 different analytes simultaneously in a single microplate well. The assay design is similar to a sandwich ELISA where the capture antibodies are pre-spotted into individual wells of a 96-well plate. Samples or standards are added which bind to the specific capture antibodies and are detected using Aushon's patented SuperSignal ELISA Femto Chemiluminescent Substrate.

In evaluating the multiple systems currently available, our laboratory has focused on the SearchLight system for several reasons. First, the assay portfolio is well aligned with many of the targets we are interested in measuring and second, the plate-based system has several operational advantages over the flow-based Luminex system, including lower maintenance costs, ease of use and simple-to-follow protocols. Notably any suitable assay may be used in the methods described herein. To date, we have used Searchlight technology to analyze 7 Phase I/II studies and one large Phase III studies (CALGB 80303). These multiplex analyses have been quality controlled to investigate ~40 analytes in various patient samples (i.e., serum, citrate plasma, EDTA plasma, and urine).

We have worked to optimize the design of customized multiplex ELISA plates via extensive collaborations with SearchLight (recently acquired by Aushon Biosystems, Inc.). Considerable effort has been devoted in developing appropriately designed panels in order to evaluate over 40 regulators of tumor and normal angiogenesis (see Table 1 above). All plate designs were optimized for use in cancer patients in order to 1) limit cross-reactivity of the antibodies 2) optimize sensitivity and specificity and 3) maximize the linearity of the assay's dynamic range.

Methods for detecting expression of the biomarkers described herein are not limited to protein expression. Gene expression profiling including methods based can hybridization analysis of polynucleotides, methods based on sequencing of polynucleotides, immunohistochemistry methods, and proteomics-based methods may also be used. The most commonly used methods known in the art for the quantification of mRNA expression in a sample include northern blotting and in situ hybridization (Parker and Barnes, Methods Mol. Biol. 106:247-83, 1999), RNAse protection assays (Hod, Biotechniques 13:852-54, 1992), PCR-based methods, such as reverse transcription PCR(RT-PCR) (Weis et al., TIG 8:263-64, 1992), and array-based methods (Schena et al., Science 270:467-70, 1995). Alternatively, antibodies may be employed that can recognize specific duplexes, including DNA duplexes, RNA duplexes, and DNA-RNA hybrid duplexes, or DNA-protein duplexes. Representative methods for sequencing-based gene expression analysis include Serial Analysis of Gene Expression (SAGE) and gene expression analysis by massively parallel signature sequencing.

The term "probe" refers to any molecule that is capable of selectively binding to a specifically intended target biomolecule, for example, a nucleotide transcript or a protein encoded by or corresponding to a biomarker. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

As used herein the term "predicting responsiveness" refers to providing a probability based analysis of how a particular subject will respond to a cancer therapy. The prediction of responsiveness is not a guarantee or absolute, only a statistically probable indication of the responsiveness of the subject. The prediction of responsiveness to a cancer therapy including a VEGF targeting agent may indicate that the subject is likely to be responsive to a cancer therapy including a VEGF targeting agent or alternatively may indicate that the subject is not likely to be responsive to a cancer therapy including a VEGF targeting agent. Alternatively, the prediction may indicate that inclusion of a VEGF targeting agent in a cancer therapy regime may be counter-productive and lead to a worse result for the subject than if no therapy was used or a placebo was used. Responsiveness includes but is not limited to, any measure of a likelihood of clinical benefit. For example, clinical benefits include an increase in overall survival, an increase in progression free survival, an increase in time to progression, increased tumor response, decreased symptoms, or other quality of life benefits.

A VEGF targeting agent includes any therapeutic agent targeting VEGF family members or any member of the VEGF receptor class of proteins. In particular, antibodies specific for VEGF, particularly VEGF-A, antibody-conjugated or other bioreagents capable of blocking VEGF mediated signaling, such as VEGF-R binding or competitive inhibitors, small molecules, aptamers, iRNAs, and other non-antibody-based therapeutic reagents. Anti-VEGF agents that are currently FDA approved include bevacizumab (Avastin™), sunitinib (Sutent™), sorafenib (Nexavar™), pazopanib (Votrient™), ranibizumab (Lucentis™), pegaptanib (Macugen™) and Axitinib (Inlyte™). Bevacizumab is a monoclonal antibody against VEGF that is FDA approved for the treatment of metastatic colorectal cancer, lung cancer, renal cell cancer, and glioblastoma. Sunitinib is a small molecule tyrosine kinase inhibitor that blocks VEGF, PDGF, and cKIT receptors; sunitinib is FDA approved for the treatment of renal cell carcinoma and GI Stromal tumors (GIST). Sorafenib is a small molecule tyrosine kinase inhibitor that blocks VEGF, PDGF, and cKIT receptors as well as the oncogene Raf; sorafenib is FDA approved for the treatment of renal cell carcinoma and hepatocellular carcinoma. Pazopanib (Votrient™) is a small molecule tyrosine kinase inhibitor that blocks VEGF, PDGF, and cKIT receptors; pazopanib is FDA approved for the treatment of renal cell carcinoma, Ranibizumab (Lucentis™) is a Fab fragment antibody that binds VEGF; ranibizumab is FDA approved for the treatment neovascular (wet) age related macular degeneration (AMD). Pegaptanib (Macugen™) is a pegylated RNA aptamer that FDA approved for the treatment neovascular (wet) age related macular degeneration (AMD). Axitinib (Inlyte™) is a small molecule tyrosine kinase inhibitor capable of inhibiting VEGFR1, VEGFR2, VEGFR3, PDGFR and cKIT that is FDA approved for treatment of renal cell carcinoma. Multiple other VEGF and other angiogenesis inhibitors are in various stages of clinical development.

The VEGF targeting agents may be used in combination with other cancer therapeutics in a cancer therapy regimen. Combination therapy does not require that multiple cancer therapeutics be administered simultaneously, but only that the subjects are treated with more than one therapeutic agent during a time span, such as one month, two months or more. For example, the VEGF targeting agent may be used in combination with DNA synthesis or DNA repair inhibitors such as nucleoside analogs. In the Examples, gemcitabine was used, but those of skill in the art will appreciate that a wide variety of cancer therapeutic agents are available and that such agents are often used in combination such that a DNA synthesis inhibitor and other classes of anticancer agents, including but not limited to, other DNA damaging agents, anti-metabolites, hormonal therapies, and signal transduction inhibitors, is combined with a VEGF targeting agent in a cancer therapy. In the Examples, the patients were treated with gemcitabine+ placebo or gemcitabine+bevacizumab.

The cancer may be selected from any cancer in which a VEGF targeting agent is being considered for therapeutic purposes. In particular, the cancer may be a solid tumor. Cancers for which predictions may be made include but are not limited to pancreatic, colorectal, liver, esophageal, gastric, small bowel, cholangiocarcinoma, lung, head and neck, thyroid, melanoma, breast, renal, bladder, ovarian, uterine, prostate, lymphomas, leukemias, neuroendocrine, glioblastoma or any other form of brain cancer.

In the methods described herein the expression level of at least one biomarker selected from ANG-2, SDF-1 and VEGF-D in a sample from the subject is determined using any one of the detection methods described above. Then the level in the sample from the subject is compared to a reference level of the biomarker. The reference level may be determined empirically such as it was in the Examples, by comparison to the levels found in a set of samples from cancer patients treated with cancer therapies including or excluding a VEGF targeting agent with known clinical outcomes for the patients. Alternatively, the reference level may be a level of the biomarker found in samples, such as plasma samples, which becomes a standard and can be used as a predictor for new samples. For example, the median cut-off levels reported in the Examples may now serve as reference levels for comparison. As noted in Table 3, the coefficients of variation were calculated for each biomarker and may be used to set reference levels. For example, a coefficient of variation of 20% would indicate that the median value could be altered by 20% and used as a reference level for the analysis.

In one embodiment, the expression level of ANG-2 and at least one of SDF-1, FGFb, OPN, HGF and VCAM-1 are determined. In this embodiment, low levels of ANG-2 in combination with either low levels of SDF-1, FGFb or VCAM-1 or high levels of OPN or HGF are predictive of lack of responsiveness of the cancer to treatment including a VEGF targeting agent. The prediction indicates unfavorability of including a VEGF targeting agent in the cancer therapy when the expression level of Ang-2 is less than 305 pg/mL (310, 320, 330, 340, 350, 400, 450, or 500 pg/mL) and the expression level of SDF-1 is less than 1100 pg/mL (1200, 1300, 1400, 1500, 1600, 1700, or 2000 pg/mL), FGFb is less than 30 pg/mL (35, 40, 45, 50, 60, 70, 80, 90, or 100 pg/mL), VCAM-1 is less than 1,700 ng/mL (1800, 1900, 2000, 2500, or 3000 ng/mL), OPN is more than 73 ng/mL, (70, 65, 60, 55, or 50 ng/mL) or HGF is more than 800 pg/mL (810, 790, 780, 770, 760, or 750 pg/mL). The lack of responsiveness to a VEGF targeting agent indicates a significant increase in clinical benefit to the subject when the subject is not treated with a VEGF targeting agent.

In another embodiment, the expression level of SDF-1 and OPN are determined. In this embodiment, high levels of SDF-1 and low levels of OPN are predictive of responsiveness to a VEGF targeting agent. The prediction favors responsiveness of the cancer to a cancer therapy including a VEGF targeting agent when the expression level of SDF-1 is more than 1100 pg/mL (1050, 1000, 950, 900, 850, or 800 pg/mL) and OPN is less than 75 ng/mL (80, 85, 90, 95, or 100 ng/mL). Responsiveness to a VEGF targeting agent indicates a significant increase in clinical benefit for subjects treated with a VEGF targeting agent.

In another embodiment, the expression level of SDF-1 and at least one of PDGF-AA, IGFBP-3, VEGF-R1 or MCP-1 are determined. In this embodiment, low levels of SDF-1 in combination with either low levels of MCP-1 or high levels of PDGF-AA, IGFBP-3, or VEGF-R1 are predictive of lack of responsiveness of the cancer to treatment including a VEGF targeting agent. The prediction indicates unfavorability of including a VEGF targeting agent in the cancer therapy when the expression level of SDF-1 is less than 1100 ng/mL (1200, 1300, 1400, 1500, 1600, 1700, or 2000 pg/mL) and the expression level of MCP-1 is less than 525 pg/mL (550, 575, 600, 650, 700, or 750 pg/mL), PDGF-AA is more than 230 pg/mL (200, 175, 150, 125, 100, 75, or 50 pg/mL), IGFBP-3 is more than 700,000 ng/mL (650,000, 600,000, 550,000, 500,000 or 450,000 ng/mL) or VEGF-R1 is more than 120 pg/mL (100, 90, 80, 70 or 60 pg/mL). Lack of responsiveness to a VEGF targeting agent indicates a significant increase in clinical benefit for subjects not treated with a VEGF targeting agent.

In another embodiment, the expression level of HGF and at least one of MCP-1 or IGF-1 are determined. In this embodiment, high levels of HGF in combination with either low levels of MCP-1 or high levels of IGF-1 are predictive of lack of responsiveness of the cancer to treatment including a VEGF targeting agent. The prediction indicates unfavorability of including a VEGF targeting agent in the cancer therapy when the expression level of HGF is more than 800 pg/mL (750, 700, 650, 600 or 550 pg/mL) and the expression level of MCP-1 is less than 525 pg/mL (550, 575, 600, 650, 700, or 750 pg/mL) or IGF-1 is more than 690 pg/mL (675, 650, 625, 600, 550, 500 pg/mL). Lack of responsiveness to a VEGF targeting, agent indicates a significant increase in clinical benefit for subjects not treated with a VEGF targeting agent.

In another embodiment, the expression level of VEGF-C and GROa are determined. In this embodiment, low levels of VEGF-C in combination with high levels of GROa are predictive of lack of responsiveness of the cancer to treatment including a VEGF targeting agent. The prediction indicates unfavorability of including a VEGF targeting agent in the cancer therapy when the expression level of VEGF-C is less than 575 pg/mL (600, 625, 650, 675, 700 or 725 pg/mL) and the expression level of GROa is more than 70 pg/mL (65, 60, 55, 50, or 45 pg/mL).

In another embodiment, low levels of VEGF-D are predictive of responsiveness to a VEGF targeting agent. In this embodiment, the prediction favors responsiveness to a cancer therapy including a VEGF targeting agent when the expression level of VEGF-D is less than 1050 pg/mL (1075, 1100, 1125, 1150, 1175, 1200, or 1250 pg/mL). Responsiveness to a VEGF targeting agent indicates a significant increase in clinical benefit for subjects treated with a VEGF targeting agent.

In another embodiment, median to high levels of VEGF-D are predictive of lack of responsiveness of the cancer to treatment including a VEGF targeting agent. The prediction is unfavorable for responsiveness to a cancer therapy including a VEGF targeting agent when the expression level of VEGF-D is more than 1100 pg/mL (1075, 1050, 1025, 1000, 950, or 900 pg/mL). Lack of responsiveness to a VEGF targeting agent indicates a significant increase in clinical benefit for subjects not treated with a VEGF targeting agent.

The predictive methods described herein may be combined to provide increased significance of the results. For example, the levels of SDF-1, ANG-2 and OPN may all be determined in a sample from the subject. The levels may be compared to the reference levels and a prediction made. The prediction is favorable for responsiveness to a cancer therapy including a VEGF targeting agent if the SDF-1 levels are high, and the OPN levels are low. Alternatively, a sample with low SDF-1 and low ANG-2 will be predictive of lack of effectiveness of a VEGF targeting agent. In another embodiment, the test may further include VEGF-D, such that inclusion of a VEGF targeting agent is predictable to be favorable if the VEGF-D and OPN levels are low and the SDF-1 levels are high. Alternatively, if the VEGF-D levels are not low, but instead are in the mid to high range as compared to the reference levels and the sample has low SDF-1 and low ANG-2, then a VEGF targeting agent will be predicted to not be effective as part of the cancer therapy.

Methods of developing a prognosis, in particular a survival or progression free survival prognosis, for a subject with pancreatic cancer is also provided herein. In one embodiment, the prognosis is independent of cancer therapeutic or cancer treatment regimen employed. In one embodiment, the subject may have localized, advanced or metastatic cancer. The method includes determining or detecting the expression level of biomarkers including IGFBP-1, PDGF-AA and at least one of IL-6 and CRP in a sample from the subject. The levels of the biomarkers present in the sample are then compared to reference levels as described above. Finally by comparison to the reference levels a prognosis for the subject can be determined.

In one embodiment, the expression levels of IGFBP-1, PDGF-AA and IL-6 or CRP are measured and low levels are indicative of a better prognosis and high levels are indicative of poor prognosis. In one embodiment, the survival prognosis for the subject is less than 6 months when the expression level of IGFBP-1 is more than 13,000 pg/mL (12,750, 12,500, 12,000, 11,000, 10,000, 9,000 pg/mL), PDGF-AA is more than 225 pg/mL (200, 175, 150, 125, 100 or 75 pg/mL) and either IL-6 is more than 15 pg/mL (12, 10, 8, or 6 pg/mL) or CRP is more than 20,000 ng/mL (19,000, 18,000, 17,000, 16,000 or 15,000 ng/mL). In another embodiment, the survival prognosis for the subject is more than 6 months when the expression level of IGFBP-1 is less than 13,500 pg/mL (13, 250, 14,000, 15,000, 16,000, 17,000 pg/mL), PDGF-AA is less than 250 pg/mL (275, 300, 325, 350 or 400 pg/mL) and either IL-6 is less than 20 pg/mL (25, 30, 40, 50, 60, or 70 pg/mL) or CRP is less than 21,000 ng/mL (22,000, 23,000, 24,000, 25,000 or 26,000 ng/mL).

In one embodiment, the expression level of IGFBP-1, PDGF-AA and CRP and the expression level of at least one of PAI-1-total and PEDF are determined and low levels are indicative of a better prognosis and high levels are indicative of a poor prognosis. The survival prognosis for the subject is less than 6 months when the expression level of IGFBP-1 is more than 13,000 pg/mL (12,750, 12,500, 12,000, 11,000, 10,000, 9,000 pg/mL), PDGF-AA is more than 225 pg/mL (200, 175, 150, 125, 100 or 75 pg/mL), CRP is more than 20,000 ng/mL (19,000, 18,000, 17,000, 16,000 or 15,000 ng/mL), PAI-1 total is more than 27,000 pg/mL (26,000, 25,000, 24,000, 23,000 or 22,000 pg/mL) and PEDF is more than 3,500 ng/mL (3250, 3000, 2750, 2500, or 2000 ng/mL). The survival prognosis for the subject is more than 6 months when the expression level of IGFBP-1 is less than 13,500 pg/mL (13,250, 14,000, 15,000, 16,000, 17,000 pg/mL). PDGF-AA is less than 250 pg/mL (275, 300, 325, 350 or 400 pg/mL), CRP is less than 21,000 ng/mL (22,000, 23,000, 24,000, 25,000 or 26,000 ng/mL), PAI-1 total is less than 28,000 pg/mL (29,000, 30,000, 31,000 or 32,000 pg/mL) and PEDF is less than 3,600 ng/mL (3750, 4000, 4250, 4500, or 5000 ng/mL). In one embodiment, the subject is being treated with gemcitabine alone.

In another embodiment, the expression level of IGFBP-1, PDGF-AA and IL-6 and at least one of PDGF-BB and TSP-2 are determined. In this embodiment, low levels of the biomarkers are indicative of a better prognosis and high levels are indicative of a poor prognosis. The survival prognosis for the subject is less than 6 months when the expression level of IGFBP-1 is more than 13,000 pg/mL (12,750, 12,500, 12,000, 11,000, 10,000, 9,000 pg/mL), PDGF-AA is more than 225 pg/mL (200, 175, 150, 125, 100 or 75 pg/mL), IL-6 is more than 15 pg/mL (12, 10, 8, or 6 pg/mL), PDGF-BB is more than 180 pg/mL (175, 150, 125, 100, or 75 pg/mL) and TSP-2 is more than 20,000 pg/mL (19,000, 18,000, 17,000, 16,000 or 15,000 pg/mL). The survival prognosis for the subject is more than 6 months when the expression level of IGFBP-1 is less than 13,500 pg/mL (13,250, 14,000, 15,000, 16,000, 17,000 pg/mL), PDGF-AA is less than 250 pg/mL (275, 300, 325, 350 or 400 pg/mL), IL-6 is less than 20 pg/mL (25, 30, 40, 50, 60, or 70 pg/mL), PDGF-BB is less than 190 pg/mL (200, 225, 250, 300, 350 or 400 pg/mL) and TSP-2 is less than 21,000 pg/mL (22,000, 23,000, 24,000, 25,000 or 26,000 pg/mL). In one embodiment, the subject is being treated with gemcitabine and a VEGF targeting agent.

In another embodiment, the expression level of at least one of ICAM-1, Ang2, IL-8, TSP-2, VCAM-1, PAI-1, and IGF-1 are determined. In this embodiment, low levels of ICAM-1, Ang2, IL-8, TSP-2, VCAM-1, or PAI-1-active as compared to the reference level are indicative of a better prognosis and high levels of ICAM-1, Ang2, IL-8, TSP-2, VCAM-1, or PAI-1-active as compared to the reference level are indicative of a poor prognosis. In this embodiment, high levels of IGF-1 as compared to the reference level is indicative of a better prognosis and low levels of IGF-1 as compared to the reference level is indicative of a poor prognosis.

In one embodiment, the survival prognosis for the subject is less than 6 months when the expression level of IGFBP-1 is more than 13,000 pg/mL (12,750, 12,500, 12,000, 11,000, 10,000, 9,000 pg/mL), or ICAM-1 is more than 350 ng/mL (300, 275, 250, 225, or 200 ng/mL), or Ang2 is more than 300 pg/mL (275, 250, 225, 200, 175 or 150 pg/mL), or CRP is more than 20,000 ng/mL (19,000, 18,000, 17,000, 16,000 or 15,000 ng/mL), or IL-8 is more than 49 pg/mL (45, 40, 35, 30 or 25 pg/mL), or IL-6 is more than 17 pg/mL (15, 12, 10, 8, or 6 pg/mL), or TSP-2 is more than 20,000 pg/mL (19,000, 18,000, 17,000, 16,000 or 15,000 pg/mL), or VCAM-1 is more than 1,600 ng/mL (1500, 1400, 1300, 1200 or 1100 ng/mL), or PAI-1-active is more than 2200 pg/mL (2100, 2000, 1900, 1800 or 1700 pg/mL), or IGF-1 is less than 700 pg/mL (750, 800, 850, 900, or 1000 pg/mL).

In one embodiment, survival prognosis for the subject is more than 6 months when the expression level of IGFBP-1 is less than 13,500 pg/mL (13,250, 14,000, 15,000, 16,000, 17,000 pg/mL), or ICAM-1 is less than 360 ng/mL (375, 400, 425, 450, 475, or 500 ng/mL), or Ang2 is less than 305 pg/mL (310, 320, 330, 340, 350, 400, 450, or 500 pg/mL), or CRP is less than 21,000 ng/mL (22,000, 23,000, 24,000, 25,000 or 26,000 ng/mL), or IL-8 is less than 50 pg/mL (55, 60, 65, 70, 75, 80 or 85 pg/mL), or IL-6 is less than 18 pg/mL (20, 25, 30, 40, 50, 60, or 70 pg/mL), or TSP-2 is less than 21,000 pg/mL (22,000, 23,000, 24,000, 25,000 or 26,000 pg/mL), or VCAM-1 is less than 1,700 ng/mL (1800, 1900, 2000, 2100 or 2200 ng/mL), or PAI-1-active is less than 2300 pg/mL (2400, 2500, 2600, 2700, 2800 or 2900 pg/mL), or IGF-1 is more than 690 pg/mL (675, 650, 625, 600, 550, 500 or 450 pg/mL).

Methods of developing a treatment plan for a subject with cancer are also provided herein. Treatment plans may be developed using the predictions of the responsiveness of the cancer to treatment with a cancer therapy including an antibody specific for VEGF-A obtained using the methods described herein to determine whether treatment of the subject with a cancer therapy including a VEGF targeting agent may be beneficial. The treatment plan will include a VEGF targeting agent if such a therapeutic is expected to be beneficial and the treatment plan will not include a VEGF targeting agent if it is not predicted to be clinically beneficial to the subject as described above.

The following examples are meant only to be illustrative and are not meant as limitations on the scope of the invention or of the appended claims. All references cited herein are hereby incorporated by reference in their entireties.

EXAMPLES

Materials and Methods

Patients:

Eligibility of patients evaluated in this correlative analysis was described previously (Kindler et al., J Clin Oncol 2010 28(22):3617-3622). Briefly, eligible patients had histologically- or cytologically-confirmed pancreatic adenocarcinoma not amenable to curative surgery. Measurable disease was not required. Prior chemotherapy for metastatic disease was not permitted. Adjuvant chemotherapy was allowed if it did not contain gemcitabine or bevacizumab, if it was given more than 4 weeks before enrollment, and if the patient had subsequent disease progression. Prior radiation was allowed if it was completed at least 4 weeks prior to enrollment and there was disease outside the radiation port. Patients were required to be at least 18 years of age and have a life expectancy of at least 12 weeks. Written informed consent was obtained from all patients participating in tins correlative analysis. Table 2 provides the demographic information for the patients.

TABLE 2

Patient Characteristics

|  | Overall Whole population | % | Overall EDTA population No. | % | Gem + Placebo No. | % | Gem + Bev No. | % |
|---|---|---|---|---|---|---|---|---|
| No. patients | 602 |  | 328 |  | 159 |  | 169 |  |
| Age, years |  |  |  |  |  |  |  |  |
| Median | 64.1 |  | 64.0 |  | 65.5 |  | 63.1 |  |
| Range | 26.3-88.7 |  | 35.8-84.2 |  | 35.8-83.7 |  | 35.9-84.2 |  |
| Gender male |  | 55 |  | 55 |  | 48 |  | 62 |
| Race white |  | 88 |  | 89 |  | 91 |  | 88 |
| ECOG PS |  |  |  |  |  |  |  |  |
| 0 |  | 37 |  | 40 |  | 39 |  | 40 |
| 1 |  | 52 |  | 50 |  | 53 |  | 48 |
| 2 |  | 11 |  | 10 |  | 8 |  | 12 |
| Extent of disease |  |  |  |  |  |  |  |  |
| Locally adv. |  | 12 |  | 12 |  | 12 |  | 12 |
| Metastatic |  | 88 |  | 88 |  | 88 |  | 88 |
| Median OS | 5.9 |  | 6.1 |  | 6.3 |  | 5.9 |  |
| (range) | (5.3-6.5) |  | (5.5-6.9) |  | (5.1-8.0) |  | (5.0-7.0) |  |
| Median PFS | 3.5 |  | 3.8 |  | 3.5 |  | 3.8 |  |
| (range) | (3.0-3.8) |  | (3.3-4.0) |  | (2.4-4.2) |  | (3.5-4.6) |  |

Treatment:

Gemcitabine (1,000 mg/m$^2$) was administered intravenously over 30 minutes on days 1, 8, and 15 of a 28-day cycle. Bevacizumab (10 mg/kg) or placebo was given intravenously after gemcitabine on days 1 and 15 of each cycle Bevacizumab or placebo dose was initially given over 90 minutes, and if no infusion reaction occurred, the second dose was given over 60 minutes, and subsequent doses were given over 30 minutes. Treatment continued until progressive disease, unacceptable toxicities, or withdrawal of consent.

Sample Collection and Analysis:

Peripheral venous blood was collected from consenting patients into lavender (EDTA anticoagulant) vacutainers for plasma isolation. The tubes were centrifuged at 2500 g for 15 minutes within 30 minutes of collection. Plasma was aliquoted into cryovials, snap frozen, and samples shipped for centralized storage at the CALGB Pathology Coordinating Office. Before analysis, all patient samples were shipped to our laboratory (Duke/CALGB Molecular Reference Lab), thawed on ice, re-aliquoted based on specific assay requirements and stored at −80° C. All assays were performed in triplicate after 2 freeze-thaw cycles only and all analysis was conducted while blinded to clinical outcome.

Thirty-two biomarkers were analyzed using Searchlight platform (Aushon Biosystems, Inc., Billerica, Mass.) following manufacturer's protocol. Markers are listed in Table 1 above. Additional ELISA assays were conducted for IGF-1 (Immunodiagnostic Systems, Inc.; Scottsdale, Ariz.) and TGFβRIII (R&D Systems, Inc.). Plasma samples were thawed on ice, centrifuged at 20,000×g for 5 min to remove precipitate and loaded onto Searchlight plates with standard protein controls. Samples and standards were incubated at room temperature for 1 hour with shaking at 950 rpm (Lab-Line Titer Plate Shaker, Model 4625, Barnstead, Dubuque, Iowa). Plates were washed three times using a plate washer (Biotek Instruments, Inc., Model ELx405, Winooski, Vt.), biotinylated secondary antibody added, and incubated for 30 min. After washes, streptavidin-HRP was added, incubated for 30 min, washed again, and SuperSignal substrate added. Images were taken within 10 min, followed by image analysis using Searchlight array analyst software.

Statistical Analysis:

Data from the 328 patients of metastatic pancreatic cancer treated with gemcitabine and bevacizumab demonstrate that the methods are highly reproducible. For 23 of 29 targets analyzed in EDTA using Search Light Technology, coefficients of variation were less than 20%. See Table 3. Both the TGFβRIII and IGF-1 assays were performed using standard ELISA procedures and had coefficients of variation below 5%.

TABLE 3

Coefficients of Variation for Analytes tested

|  | Analyte | Average CV |
|---|---|---|
| 1 | TGFβ-RIII | 2.60 |
| 2 | IGF-1 | 3.73 |
| 3 | P-selectin | 7.46 |
| 4 | IGFBP-3 | 7.94 |
| 5 | HGF | 8.12 |
| 6 | TSP-2 | 8.76 |
| 7 | SDF-1 | 9.44 |
| 8 | VCAM-1 | 10.01 |
| 9 | PAI1 total | 10.07 |
| 10 | MCP-1 | 10.37 |
| 11 | VEGF-D | 10.69 |

TABLE 3-continued

Coefficients of Variation for Analytes tested

| | Analyte | Average CV |
|---|---|---|
| 12 | IL-6 | 10.72 |
| 13 | PAI1 active | 11.30 |
| 14 | PDGF-BB | 12.21 |
| 15 | TGFβ1 | 12.48 |
| 16 | VEGF-R1 | 13.25 |
| 17 | ICAM-1 | 14.42 |
| 18 | IGFBP-1 | 14.46 |
| 19 | PEDF | 14.68 |
| 20 | ANG2 | 14.75 |
| 21 | VEGF-R2 | 14.89 |
| 22 | TGFβ2 | 15.20 |
| 23 | PDGF-AA | 17.69 |
| 24 | VEGF | 17.90 |
| 25 | VEGF-C | 19.01 |
| 26 | FGFb | 20.09 |
| 27 | PLGF | 22.11 |
| 28 | OPN | 22.98 |
| 29 | GROα | 24.26 |
| 30 | IL-8 | 24.70 |
| 31 | CRP | 27.34 |

Patterns of expression were analyzed at baseline and were correlated with overall survival (OS) and progression free survival (PFS) using univariate Cox proportional hazard regression models and multivariate Cox models with leave-one-out cross validation. Spearman's rank correlation coefficients were calculated for all pairs of analytes. Unsupervised hierarchical clustering of analytes was also performed to produce dendrogram plots. Data indicate that several analyte clusters reflect known biological categories. This data is summarized in FIG. 1 below.

Prior to statistical analysis, all data was initially reviewed for accuracy and quality. Any study samples that fell outside the linear portion of the standard curve were retested. Samples that read below the limit of detection were retested at a lower dilution, if possible. Samples that read above the linear portion of the standard curve were serially diluted and retested to obtain accurate measurements. Any analyte that did not meet the aforementioned criteria resulted in the sample being re-evaluated. In the case of samples reading below the assay's limit of detection that cannot be re-assayed, we have developed imputation methods to derive a number for such allowing for inclusion into our statistical approaches.

The primary endpoint of interest will be overall survival (OS) with correlation to the blood analytes; however, progression-free survival (PFS) was evaluated. Cox regression analysis was performed to assess the prognostic value of blood analytes for the clinical endpoints of interest. For each analyte, univariate Cox regression analysis was performed to assess the associations with OS and PFS ($\alpha=0.01$). Cox regression models were performed for Gem+Placebo and Gem+Bev separately. Raw, continuous analytes intensities for baseline measures were used. Summary statistics included the hazard ratios and associated confidence intervals. For each analyte, the inclusion of potential confounding factors was explored. These factors included; gender, extent of disease (locally advanced vs metastatic), age (continuous), and performance status (0, 1, 2).

For PFS and OS, prognostic models were built with multivariate Cox regression analysis using the most informative analytes chosen from leave-one-out cross-validation for Gem+Placebo and Gem+Bev separately. At each leave-one-out iteration, the training samples were used to build a Cox regression model for predicting the survival of the testing samples. The predicted survival times were used to split the groups in half into high and low risk groups. Kaplan-Meier estimates of the hazard profiles for these two groups were produced.

Results

Baseline Characteristics

Out of the 602 patients who accrued to the parent protocol, baseline EDTA plasma samples were available on 328 patients, 159 pts in the gemcitabine/placebo group and 169 in the gemcitabine/bevacizumab group. The clinical characteristics and outcomes of these patients were similar to those on the parent study. Additionally, the two cohorts in this correlative study had similar characteristics across both groups, except for a minor imbalance in gender (Table 2 above).

Angiome Factor Measurement and Correlation

Thirty-one factors related to angiogenesis, inflammation, and coagulation were evaluated; standard ELISAs were used to evaluate IGF-1 and TGFβRIII while the SearchLight system (Aushon BioSystems) was used to evaluate the remaining analytes. Multiplex analyses demonstrated good sensitivity and coefficient's of variation (CVs) were generally in the range of 10-30%. (Table 3). Only 2 analytes (PlGF and bFGF) had levels below the limits of quantification for greater than 10% of patients evaluated.

The median and range (high/low) for all analytes at baseline are provided in Table 4. Analyte values are presented in pg/mL or ng/mL, unless otherwise noted and data is provided for the study as a whole, as well as separated based on assigned cohort (trt 1=bevacizumab-treated cohort; trt 2=placebo control cohort).

TABLE 4

Analyte concentrations measured including Median and Range

| | | | Baseline | | |
|---|---|---|---|---|---|
| Analyte | trt | N | Median | Min | Max |
| Ang2 (pg/mL) | All | 328 | 301.42 | 9.85 | 3150.67 |
| Ang2 (pg/mL) | 1 | 169 | 294.33 | 9.85 | 2761.5 |
| Ang2 (pg/mL) | 2 | 159 | 308.33 | 25.5 | 3150.67 |
| CRP (ng/mL) | All | 328 | 20178.5 | 14.2 | 942048 |
| CRP (ng/mL) | 1 | 169 | 23506 | 14.2 | 942048 |
| CRP (ng/mL) | 2 | 159 | 18406 | 31 | 854967 |
| FGFb (pg/mL) | All | 328 | 25.6 | 0.86 | 1120.6 |
| FGFb (pg/mL) | 1 | 169 | 23.93 | 0.86 | 1120.6 |
| FGFb (pg/mL) | 2 | 159 | 27.18 | 0.86 | 511.33 |
| GROα (pg/mL) | All | 328 | 70.8 | 7.33 | 769 |
| GROα (pg/mL) | 1 | 169 | 75.47 | 7.33 | 769 |
| GROα (pg/mL) | 2 | 159 | 62.27 | 7.6 | 448.4 |
| HGF (pg/mL) | All | 328 | 817.37 | 251.6 | 100900 |
| HGF (pg/mL) | 1 | 169 | 842.53 | 251.6 | 57834 |
| HGF (pg/mL) | 2 | 159 | 782 | 267.13 | 100900 |
| ICAM-1 (ng/mL) | All | 328 | 354.97 | 2.83 | 2498.68 |
| ICAM-1 (ng/mL) | 1 | 169 | 365.2 | 2.83 | 2498.68 |
| ICAM-1 (ng/mL) | 2 | 159 | 337.7 | 22.8 | 1811.95 |
| IGFBBP-3 (ng/mL) | All | 328 | 709577 | 4216.67 | 2184373 |
| IGFBBP-3 (ng/mL) | 1 | 169 | 713357 | 4216.67 | 1795190 |
| IGFBBP-3 (ng/mL) | 2 | 159 | 699490 | 22260 | 2184373 |
| IGFBP-1 (pg/mL) | All | 328 | 13253.3 | 86.67 | 1028290 |
| IGFBP-1 (pg/mL) | 1 | 169 | 13016.7 | 546.67 | 1028290 |
| IGFBP-1 (pg/mL) | 2 | 159 | 14010 | 86.67 | 190060 |
| IGF-1 (pg/mL) | All | 328 | 697.02 | 56.64 | 3398.03 |
| IGF-1 (pg/mL) | 1 | 169 | 704.51 | 56.64 | 3398.03 |
| IGF-1 (pg/mL) | 2 | 159 | 637.25 | 126.34 | 1768.5 |
| IL-6 (pg/mL) | All | 328 | 17.47 | 2.8 | 1105.33 |
| IL-6 (pg/mL) | 1 | 169 | 17.73 | 2.8 | 1105.33 |
| IL-6 (pg/mL) | 2 | 159 | 17.2 | 3.07 | 691.2 |
| IL-8 (pg/mL) | All | 328 | 49.2 | 0.59 | 2061.93 |
| IL-8 (pg/mL) | 1 | 169 | 47.33 | 0.6 | 2061.93 |
| IL-8 (pg/mL) | 2 | 159 | 52.47 | 0.59 | 757.87 |
| MCP-1 (pg/mL) | All | 328 | 521.75 | 146.67 | 3445.5 |
| MCP-1 (pg/mL) | 1 | 169 | 526.33 | 159 | 1653.67 |

TABLE 4-continued

Analyte concentrations measured including Median and Range

| | | Baseline | | | |
|---|---|---|---|---|---|
| Analyte | trt | N | Median | Min | Max |
| MCP-1 (pg/mL) | 2 | 159 | 517 | 146.67 | 3445.5 |
| OPN (ng/mL) | All | 328 | 74.06 | 1.55 | 1036.38 |
| OPN (ng/mL) | 1 | 169 | 75.55 | 1.55 | 1036.38 |
| OPN (ng/mL) | 2 | 159 | 69.32 | 1.56 | 292.35 |
| PAI1-act (pg/mL) | All | 328 | 2295.2 | 3.8 | 31039.47 |
| PAI1-act (pg/mL) | 1 | 169 | 2110.33 | 3.8 | 29658.27 |
| PAI1-act (pg/mL) | 2 | 159 | 2517.73 | 121.07 | 31039.47 |
| PAI1-tot (pg/mL) | All | 328 | 27861.7 | 175.77 | 259313.3 |
| PAI1-tot (pg/mL) | 1 | 169 | 29570 | 175.77 | 259313.3 |
| PAI1-tot (pg/mL) | 2 | 159 | 25866.7 | 5230 | 189496.7 |
| PDGF-AA (pg/mL) | All | 328 | 239.2 | 0.47 | 5746.8 |
| PDGF-AA (pg/mL) | 1 | 169 | 242.13 | 0.47 | 5746.8 |
| PDGF-AA (pg/mL) | 2 | 159 | 219.93 | 14.87 | 3544.67 |
| PDGFbb (pg/mL) | All | 328 | 185.4 | 0.27 | 2226.47 |
| PDGFbb (pg/mL) | 1 | 169 | 183.33 | 0.27 | 2226.47 |
| PDGFbb (pg/mL) | 2 | 159 | 190.27 | 5.85 | 1386.13 |
| PEDF (pg/mL) | All | 328 | 3549283 | 2636.55 | 7855183 |
| PEDF (pg/mL) | 1 | 169 | 3562750 | 2636.55 | 7855183 |
| PEDF (pg/mL) | 2 | 159 | 3496300 | 225900 | 7364000 |
| P-Selectin (ng/mL) | All | 328 | 53.59 | 3.63 | 624.47 |
| P-Selectin (ng/mL) | 1 | 169 | 52.61 | 3.63 | 624.47 |
| P-Selectin (ng/mL) | 2 | 159 | 54.27 | 8.64 | 376.42 |
| PlGF (pg/mL) | All | 328 | 5 | 0.13 | 363.13 |
| PlGF (pg/mL) | 1 | 169 | 4.8 | 0.13 | 363.13 |
| PlGF (pg/mL) | 2 | 159 | 5.4 | 0.27 | 186.67 |
| SDF-1 (pg/mL) | All | 328 | 1103.03 | 11.25 | 36383.73 |
| SDF-1 (pg/mL) | 1 | 169 | 1126.93 | 11.25 | 36383.73 |
| SDF-1 (pg/mL) | 2 | 159 | 1021 | 88.6 | 5769 |
| TGFβ1 (pg/mL) | All | 326 | 36239.2 | 37.83 | 206971.7 |
| TGFβ1 (pg/mL) | 1 | 168 | 37178.3 | 37.83 | 206971.7 |
| TGFβ1 (pg/mL) | 2 | 158 | 32958.3 | 3818.33 | 192765 |
| TGFβ2 (pg/mL) | All | 328 | 56.73 | 5.6 | 1286.87 |
| TGFβ2 (pg/mL) | 1 | 169 | 56.73 | 8.73 | 440.93 |
| TGFβ2 (pg/mL) | 2 | 159 | 56.73 | 5.6 | 1286.87 |
| TGFβ-R3 (pg/mL) | All | 328 | 410.59 | 4.64 | 1011.55 |
| TGFβ-R3 (pg/mL) | 1 | 169 | 411.15 | 4.64 | 1011.55 |
| TGFβ-R3 (pg/mL) | 2 | 159 | 408.59 | 104.13 | 902.08 |
| TSP-2 (pg/mL) | All | 328 | 20689.1 | 1528.5 | 451368.7 |
| TSP-2 (pg/mL) | 1 | 169 | 22708.7 | 1528.5 | 451368.7 |
| TSP-2 (pg/mL) | 2 | 159 | 19353.5 | 5776 | 224395 |
| VCAM-1 (pg/mL) | All | 328 | 1614000 | 880 | 7971367 |
| VCAM-1 (pg/mL) | 1 | 169 | 1621583 | 880 | 7199817 |
| VCAM-1 (pg/mL) | 2 | 159 | 1599333 | 225900 | 7971367 |
| VEGF (pg/mL) | All | 328 | 89.57 | 1.91 | 12678.2 |
| VEGF (pg/mL) | 1 | 169 | 95.93 | 1.91 | 12678.2 |
| VEGF (pg/mL) | 2 | 159 | 82.47 | 1.91 | 3090.2 |
| VEGF-C (pg/mL) | All | 328 | 572.37 | 10.2 | 34037.87 |
| VEGF-C (pg/mL) | 1 | 169 | 588.53 | 10.2 | 34037.87 |
| VEGF-C (pg/mL) | 2 | 159 | 554.3 | 44.19 | 4732.27 |
| VEGF-D (pg/mL) | All | 328 | 1558.1 | 70.31 | 25382.27 |
| VEGF-D (pg/mL) | 1 | 169 | 1574.07 | 70.31 | 13233.27 |
| VEGF-D (pg/mL) | 2 | 159 | 1553.73 | 159.93 | 25382.27 |
| VEGF-R1 (pg/mL) | All | 328 | 122.97 | 8.2 | 43692.6 |
| VEGF-R1 (pg/mL) | 1 | 169 | 130.33 | 8.2 | 16940.47 |
| VEGF-R1 (pg/mL) | 2 | 159 | 112.93 | 1253 | 43692.6 |
| VEGF-R2 (pg/mL) | All | 328 | 3790.5 | 34.17 | 39032.83 |
| VEGF-R2 (pg/mL) | 1 | 169 | 3806.67 | 34.17 | 39032.83 |
| VEGF-R2 (pg/mL) | 2 | 159 | 3731.33 | 826.33 | 35116.17 |

To identify patterns of expression among analytes, Spearmen correlations were performed on all analytes and the following dendrogram was generated (FIG. 1). Interesting and biologically relevant associations were noted. These include associations within the VEGF/PDGF families, as well as a broader association observed for multiple inflammatory markers. Strong correlation coefficients (>0.70) were noted for only two pairs of analytes; TGFβ1 and PDGF-AA (0.76), CRP and IL-6 (0.72).

Prognostic Marker Identification

Univariate and multivariate Cox regression models were used to identify markers with statistically significant prognostic impact. Due to observed treatment-by-analyte interactions, both univariate and multivariate prognostic analyses were conducted separately for the gemcitabine/placebo and the gemcitabine/bevacizumab groups. In the univariate analysis, IGFBP-1, Ang-2, CRP, IL-8, TSP-2, VCAM-1, PAI1 active, IGF-1, PAI1-total and P-selectin were significantly correlated with overall survival in the gemcitabine/placebo group (Table 5), In the univariate analysis, IGFBP-1, ICAM-1, Ang-2, CRP, IL-8, TSP-2, VCAM-1, PAI1 active, and IGF-1 were significantly correlated with progression free survival in the gemcitabine/placebo group (Table 6). All markers remained significant (p<0.05) after accounting for multiple parameter testing using bonferroni correction methodologies.

TABLE 5

Baseline Univariate EDTA Prognostic Markers for Gem + Placebo (OS)

| | | <median | | >median | | <med vs >med | |
|---|---|---|---|---|---|---|---|
| | p-value* | Median Survival | 95% CI | Median Survival | 95% CI | Hazard ratio | 95% CI |
| IGFBP-1 | 1.2E−10 | 9.2 | (7.3, 9.9) | 4.3 | (3.1, 5.7) | 1.7 | (1.2, 2.4) |
| ICAM-1 | 7.8E−08 | 8.4 | (6.1, 9.7) | 4.8 | (3.5, 6.8) | 1.4 | (1.01, 1.90) |
| Ang2 | 1.5E−07 | 9.6 | (7.7, 10.4) | 4.6 | (3.3, 5.8) | 2.4 | (1.7, 3.3) |
| CRP | 6.9E−07 | 9.7 | (8.1, 10.6) | 3.8 | (2.9, 4.8) | 2.3 | (1.6, 3.1) |
| IL-8 | 0.000013 | 8.7 | (6.1, 9.7) | 5.0 | (3.5, 6.9) | 1.3 | (0.98, 1.86) |
| TSP-2 | 0.00007 | 9.0 | (6.8, 9.7) | 4.6 | (3.3, 5.6) | 1.6 | (1.1, 2.1) |
| VCAM-1 | 0.00021 | 9.0 | (6.7, 9.7) | 4.8 | (3.6, 5.9) | 1.6 | (1.2, 2.3) |
| PAI1-act | 0.00043 | 8.1 | (6.7, 9.2) | 4.8 | (3.4, 5.9) | 1.3 | (0.94, 1.77) |
| IGF-1 | 0.0012 | 4.2 | (3.3, 5.6) | 9.0 | (6.8, 9.7) | 0.65 | (0.47, 0.89) |
| PAI1-tot | 0.004 | 7.4 | (5.9, 9.6) | 4.6 | (3.3, 7.7) | 1.3 | (0.98, 1.84) |
| P-Selectin | 0.0062 | 8.5 | (5.8, 9.9) | 5.7 | (3.9, 6.8) | 1.6 | (1.1, 2.1) |

Above is a list of analytes that is prognostic univariately for overall survival using the Cox Proportional Hazard model. On the right hand side, it indicates the median survival time and its 95% CI for less than median and greater than median level of the analytes. All analytes presented remain significant (p < 0.05) after accounting for multiple parameter testing using bonferroni correction methods.
*from Cox proportional hazard model using continuous analyte values.

TABLE 6

Univariate Progression-Free Survival Prognostic Markers at baseline (EDTAs) for Gem + Placebo

|  | p-value* | <median Median Survival | <median 95% CI | >median Median Survival | >median 95% CI | <med vs >med Hazard ratio | <med vs >med 95% CI |
|---|---|---|---|---|---|---|---|
| IGFBP-1 | 0.00001 | 4.2 | (3.5, 5.6) | 2.5 | (2.0, 3.9) | 1.4 | (1.1, 2.0) |
| ICAM-1 | 6.9E−07 | 4.0 | (2.8, 5.5) | 2.8 | (2.0, 4.2) | 1.2 | (0.85, 1.62) |
| Ang2 | 0.000046 | 4.9 | (3.3, 5.6) | 2.2 | (2.0, 3.9) | 1.7 | (1.2, 2.3) |
| CRP | 0.00013 | 5.5 | (4.1, 5.8) | 2.1 | (1.8, 2.8) | 2.1 | (1.5, 2.9) |
| IL-8 | 0.000017 | 4.6 | (3.7, 5.5) | 2.3 | (2.0, 3.6) | 1.3 | (0.97, 1.8) |
| TSP-2 | 0.0043 | 4.1 | (2.7, 5.5) | 2.9 | (2.1, 4.2) | 1.6 | (1.1, 2.1) |
| VCAM-1 | 0.002 | 4.7 | (2.7, 5.8) | 2.8 | (2.1, 3.9) | 1.7 | (1.2, 2.3) |
| PAI1-act | 0.046 | 4.2 | (2.9, 5.5) | 2.5 | (2.0, 4.0) | 1.2 | (0.88, 1.67) |
| IGF-1 | 0.006 | 2.4 | (2.0, 3.9) | 4.6 | (3.5, 5.6) | 0.69 | (0.50, 0.94) |

Above is a list of analytes that is prognostic univariately for overall survival using the Cox Proportional Hazard model. On the right hand side, it indicates the median survival time and its 95% CI for less than median and greater than median level of the analytes. All analytes presented remain significant (p < 0.05) after accounting for multiple parameter testing using bonferroni correction methods.
*from Cox proportional hazard model using continuous analyte values.

TSP-2, CRP, IL-6, IGFBP-1, Ang-2, ICAM-1, VCAM-1, and IGF-1 were significantly correlated with overall survival in the gemcitabine/bevacizumab group (Table 7). TSP-2, CRP, IL-6, IGFBP-1, Ang-2, ICAM-1, and VCAM-1 were significantly correlated with progression free survival in the gemcitabine/bevacizumab group (Table 8). It should be noted that high consistency was observed across both cohorts. All of these factors were unfavorable prognostic markers, where higher levels were associated with a less favorable outcome. The only notable exception was IGF-1, where higher levels were associated with a more favorable outcome. Additionally, all of these markers remained prognostic after correction for known clinical prognostic variables, including age, race, gender and performance status. Tables 9 and 10 are composite lists of analytes that are prognostic for overall survival and progression free survival irrespective of treatment condition, respectively.

TABLE 7

Baseline Univariate EDTA Prognostic Markers for Gem + Bevacizumab (OS)

|  | p-value* | <median Median Survival | <median 95% CI | >median Median Survival | >median 95% CI | <med vs >med Hazard ratio | <med vs >med 95% CI |
|---|---|---|---|---|---|---|---|
| TSP-2 | 2.6E−08 | 6.1 | (5.2, 7.4) | 5.7 | (4.1, 7.1) | 1.3 | (0.9, 1.7) |
| CRP | 2.7E−08 | 7.4 | (5.9, 9.5) | 4.6 | (3.5, 5.8) | 1.9 | (1.4, 2.6) |
| IL-6 | 1.4E−07 | 8.4 | (7.0, 9.7) | 3.8 | (3.1, 4.8) | 2.3 | (1.7, 3.2) |
| IGFBP-1 | 8.3E−07 | 8.0 | (6.5, 9.7) | 4.1 | (3.2, 5.3) | 2.2 | (1.6, 3.0) |
| Ang2 | 1.7E−06 | 7.0 | (5.5, 15.0) | 4.8 | (3.8, 6.5) | 1.4 | (1.1, 2.0) |
| ICAM-1 | 0.00027 | 6.8 | (5.5, 8.3) | 5.0 | (4.0, 6.8) | 1.5 | (1.1, 2.0) |
| VCAM-1 | 0.0012 | 7.1 | (5.5, 8.1) | 5.3 | (4.1, 6.5) | 1.5 | (1.1, 2.0) |
| IGF-1 | 0.0019 | 4.8 | (3.7, 5.9) | 7.1 | (5.7, 8.1) | 0.72 | (0.53, 0.97) |

Above is a list of analytes that is prognostic univariately for overall survival using the Cox Proportional Hazard model. On the right hand side, it indicates the median survival time and its 95% CI for less than median and greater than median level of the analytes. All analytes presented remain significant (p < 0.05) after accounting for multiple parameter testing using bonferroni correction methods.
*from Cox proportional hazard model using continuous analyte values.

TABLE 8

Univariate Progression-Free Survival Prognostic Markers at baseline (EDTAs) for Gem + Bev

|  | p-value* | <median Median Survival | <median 95% CI | >median Median Survival | >median 95% CI | <med vs >med Hazard ratio | <med vs >med 95% CI |
|---|---|---|---|---|---|---|---|
| TSP-2 | 0.00000035 | 3.8 | (3.5, 5.7) | 3.8 | (2.8, 5.0) | 1.2 | (0.88, 1.64) |
| CRP | 0.0000075 | 5.5 | (3.8, 7.0) | 3.3 | (2.1, 3.9) | 1.7 | (1.3, 2.3) |
| IL-6 | 0.0003 | 6.1 | (5.0, 7.3) | 2.4 | (2.0, 3.8) | 2.3 | (1.7, 3.1) |
| IGFBP-1 | 0.000018 | 5.5 | (3.8, 7.0) | 3.0 | (2.0, 3.8) | 1.7 | (1.3, 2.3) |
| Ang2 | 0.0000068 | 5.3 | (3.8, 6.9) | 3.1 | (2.0, 4.0) | 1.4 | (1.002, 1.85) |

TABLE 8-continued

Univariate Progression-Free Survival Prognostic Markers at baseline (EDTAs) for Gem + Bev

|  | p-value* | <median Median Survival | 95% CI | >median Median Survival | 95% CI | <med vs >med Hazard ratio | 95% CI |
|---|---|---|---|---|---|---|---|
| ICAM-1 | 0.000044 | 4.3 | (3.7, 6.4) | 3.7 | (2.5, 4.1) | 1.4 | (1, 1.84) |
| VCAM-1 | 0.014 | 3.9 | (3.7, 6.2) | 3.8 | (2.5, 4.8) | 1.3 | (0.98, 1.82) |

Above is a list of analytes that is prognostic univariately for progression free survival using the Cox Proportional Hazard model. On the right hand side, it indicates the median survival time and its 95% CI for less than median and greater than median level of the analytes. All analytes presented remain significant (p < 0.05) after accounting for multiple parameter testing using bonferroni correction methods.
*from Cox proportional hazard model using continuous analyte values

TABLE 9

Univariate Overall Survival Prognostic Markers at baseline (EDTAs) for Gem-based treatments

|  | p-value* | <median Median Survival | 95% CI | >median Median Survival | 95% CI | <med vs >med Hazard ratio | 95% CI |
|---|---|---|---|---|---|---|---|
| CRP | 3E−14 | 8.7 | (7.4, 9.7) | 4.4 | (3.6, 5.0) | 2.1 | (1.7, 2.6) |
| Ang2 | 1.3E−13 | 8.1 | (6.9, 9.5) | 4.6 | (3.8, 5.9) | 1.8 | (1.4, 2.2) |
| IGFBP-1 | 1.4E−12 | 8.7 | (7.3, 9.7) | 4.2 | (3.4, 5.0) | 1.9 | (1.6, 2.4) |
| TSP-2 | 4.9E−12 | 7.3 | (6.1, 9.1) | 5.0 | (4.2, 6.5) | 1.4 | (1.1, 1.8) |
| ICAM-1 | 1.5E−10 | 7.3 | (6.4, 9.0) | 4.9 | (4.3, 6.3) | 1.4 | (1.1, 1.8) |
| IL-6 | 6E−8 | 9.3 | (8.3, 9.9) | 3.8 | (3.2, 4.6) | 2.4 | (1.9, 3.0) |
| VCAM-1 | 8E−7 | 7.5 | (6.9, 9.1) | 5.0 | (4.3, 5.9) | 1.6 | (1.3, 1.9) |
| IGF-1 | 0.000027 | 4.6 | (3.7, 5.4) | 7.4 | (6.7, 8.6) | 0.68 | (0.55, 0.85) |
| PAI1-act | 0.00011 | 7.2 | (6.5, 8.4) | 5.0 | (4.1, 5.9) | 1.3 | (1.04, 1.61) |
| P-Selectin | 0.0019 | 7.4 | (6.1, 9.1) | 5.4 | (4.7, 6.3) | 1.5 | (1.2, 1.8) |
| OPN | 0.0039 | 8.1 | (6.8, 9.5) | 4.8 | (4.3, 5.9) | 1.5 | (1.2, 1.8) |
| MCP-1 | 0.0077 | 7.4 | (6.4, 9.1) | 4.8 | (4.1, 6.0) | 1.4 | (1.1, 1.7) |
| PAI1-tot | 0.0081 | 7.1 | (6.0, 9.0) | 4.8 | (4.1, 6.5) | 1.4 | (1.1, 1.7) |

Above is a list of analytes that is prognostic univariately for progression free survival using the Cox Proportional Hazard model. On the right hand side, it indicates the median survival time and its 95% CI for less than median and greater than median level of the analytes. All analytes presented remain significant (p < 0.05) after accounting for multiple parameter testing using bonferroni correction methods.
*from Cox proportional hazard model using continuous analyte values

TABLE 10

Univariate Progression-Free Survival Prognostic Markers at baseline (EDTAs) for Gem-based treatment

|  | p-value* | <median Median Survival | 95% CI | >median Median Survival | 95% CI | <med vs >med Hazard ratio | 95% CI |
|---|---|---|---|---|---|---|---|
| CRP | 5.8E−09 | 5.5 | (4.0, 5.8) | 2.4 | (2.1, 3.3) | 1.9 | (1.5, 2.3) |
| Ang2 | 5.6E−10 | 5.2 | (3.8, 5.7) | 2.5 | (2.1, 3.7) | 1.5 | (1.2, 1.8) |
| IGFBP-1 | 4.6E−10 | 4.8 | (3.9, 5.7) | 2.7 | (2.1, 3.7) | 1.6 | (1.3, 2.0) |
| TSP-2 | 1.4E−08 | 3.9 | (3.5, 5.5) | 3.5 | (2.5, 4.0) | 1.3 | (1.07, 1.67) |
| ICAM-1 | 1E−10 | 4.0 | (3.7, 5.5) | 3.3 | (2.5, 3.9) | 1.3 | (1.01, 1.57) |
| IL-6 | 0.00062 | 5.5 | (4.8, 6.3) | 2.2 | (2.0, 2.9) | 2.3 | (1.8, 2.9) |
| VCAM-1 | 0.000052 | 4.4 | (3.7, 5.6) | 3.3 | (2.5, 3.9) | 1.5 | (1.2, 1.9) |
| IGF-1 | 0.0093 | 2.9 | (2.3, 3.8) | 4.1 | (3.8, 5.5) | 0.79 | (0.64, 0.99) |
| PAI1-act | 0.0071 | 3.9 | (3.7, 5.5) | 3.3 | (2.3, 4.0) | 1.3 | (1.002, 1.55) |
| P-Selectin | 0.1 | 3.9 | (3.4, 5.4) | 3.7 | (2.5, 4.0) | 1.3 | (1.06, 1.64) |
| OPN | 0.012 | 3.9 | (3.5, 5.5) | 3.5 | (2.8, 4.0) | 1.3 | (1.04, 1.63) |
| MCP-1 | 0.000098 | 3.9 | (3.5, 5.5) | 3.4 | (2.4, 4.0) | 1.2 | (1.00, 1.55) |
| PAI1-tot | 0.14 | 3.9 | (3.6, 5.5) | 3.4 | (2.6, 4.0) | 1.2 | (0.94, 1.45) |

Figure 2:
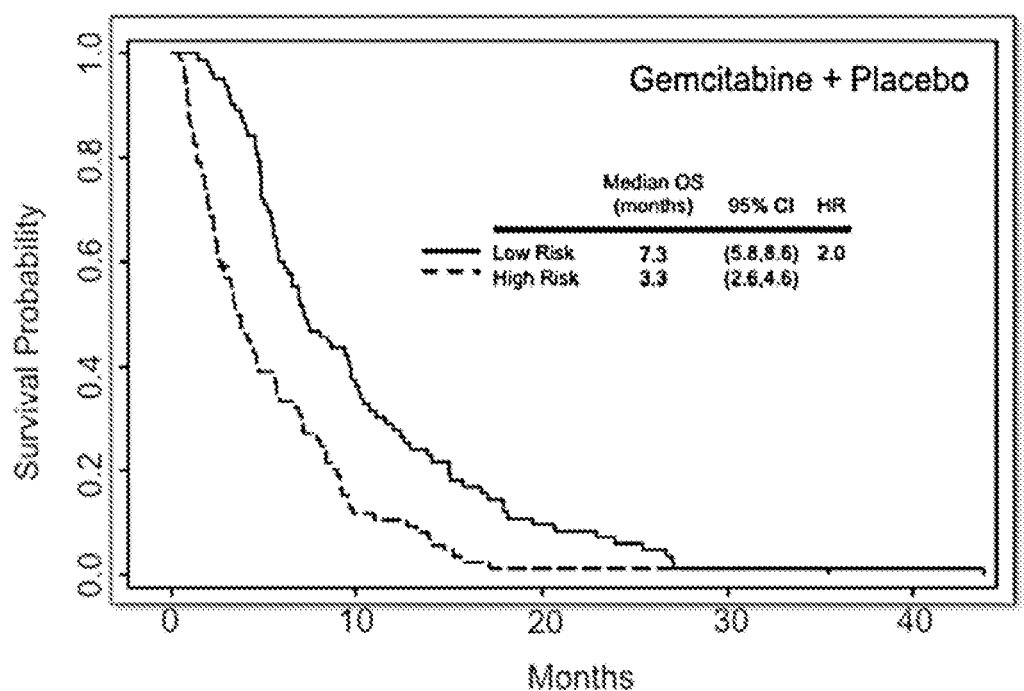
FIG. 2 is a set of Kaplan-Meier plots showing the survival data for the gemcitabine+placebo model (FIG. 2A) and the gemcitabine+bevacizumab model (FIG. 2B). The high risk groups from the multivariate analysis for each is shown in solid lines and the low risk group is shown in dashed lines.
Figure 2:
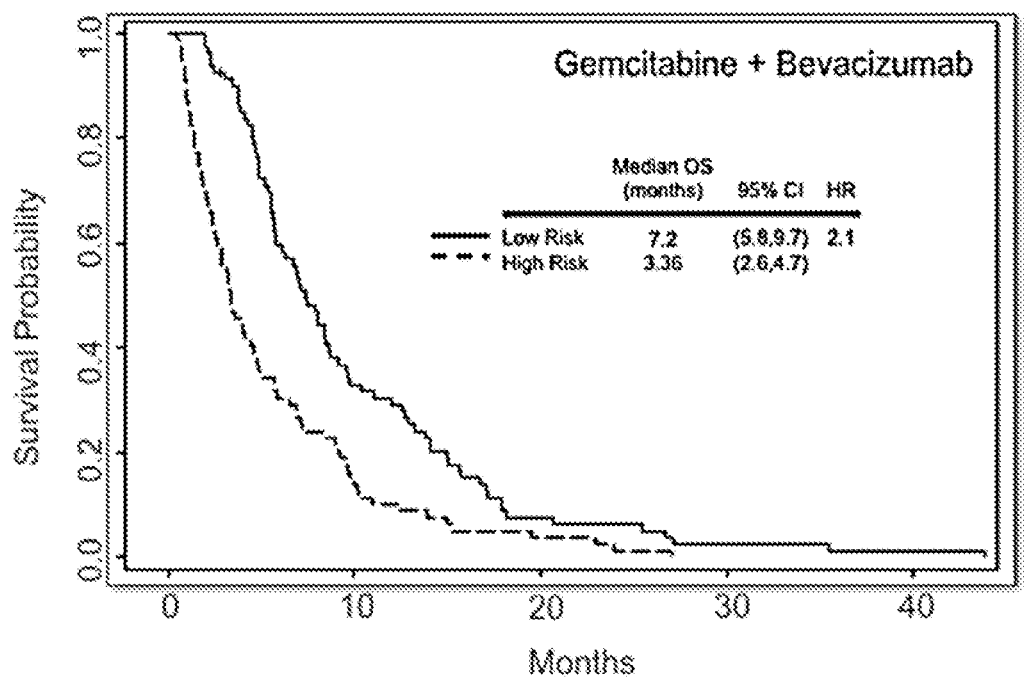

Above is a list of analytes that is prognostic univariately for progression free survival using the Cox Proportional Hazard model. On the right hand side, it indicates the median survival time and its 95% CI for less than median and greater than median level of the analytes. All analytes presented remain significant (p < 0.05) after accounting for multiple parameter testing using bonferroni correction methods.
*from Cox proportional hazard model using continuous analyte values Multivariate prognostic models for OS (and PFS) were developed using a leave one out, cross-validation approach. Using this methodology, two 5-analyte models for risk were developed, one for the gemcitabine+placebo cohort, and another for gemcitabine+bevacizumab cohort (see Table 11). The gemcitabine+placebo model for OS consisted of IGFBP-1, CRP, PDGF-AA, PAI1-total, and PEDF. This model was associated with a hazard ratio of 2.0, with corresponding median survivals of 3.3 and 7.3 months for the high and low risk groups, respectively. The gemcitabine+bevacizumab model consisted of IGFBP-1, IL-6, PDGF-AA, PDGF-BB, and TSP-2, This model was associated with a hazard ratio of 2.1, with corresponding median survivals of 3.6 and 7.2 months for the high and low risk groups, respectively. All analytes appeared in greater than 95% of the models derived during analysis. Furthermore, analytes were observed to be consistent across the models. This data is represented in the Kaplan-Meier plots shown in FIG. 2. For both the gemcitabine+placebo model (panel A) and the gemcitabine+bevacizumab model (panel B) the high-risk groups are shown in solid lines, while the low risk groups are shown in dashed lines. In both cases, an approximate two-fold change in median survival was noted.

TABLE 11

Baseline Multivariate EDTA Prognostic Models for Gem + Placebo and Gem + Bev (OS)

| Models | analytes | p-value | HR | 95% CI | High risk group | | | Low risk group | | |
|---|---|---|---|---|---|---|---|---|---|---|
| | | | | | N/(cen) | Median Survival | 95% CI | N/(cen) | Median Survival | 95% CI |
| Gem + Placebo | IGFBP-1 CRP PDGF-AA PAI-1 total PEDF | <.0001 | 2.0 | (1.4, 2.7) | 79 (0) | 3.3 | (2.6, 4.6) | 79 (1) | 7.3 | (5.8, 8.6) |
| Gem + Bev | IGFBP-1 IL-6 PDGF-AA PDGF-BB TSP-2 | <.0001 | 2.1 | (1.5, 2.8) | 85 (1) | 3.6 | (2.6, 4.7) | 83 (0) | 7.2 | (5.8, 9.7) |

(cen) = censored

Predictive Marker Identification

Figure 3:
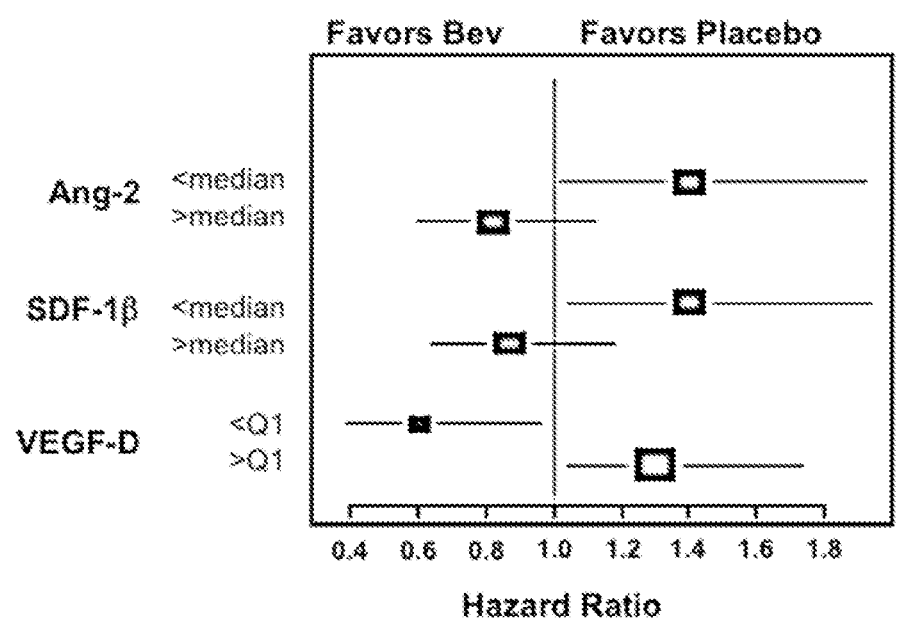
FIG. 3 is a graph showing the hazard ratio plot for each of the biomarkers identified in the univariate analysis as predictive of responsiveness or lack thereof when treated with bevacizumab.

Predictive markers were identified using the Cox proportional hazards model. Analyte values were evaluated at both median and quartile cutpoints. Three markers were identified as being predictive for bevacizumab benefit (or lack of benefit); VEGF-D, SDF1, and Ang-2. See Table 12. We observed that low levels (below median) of both Ang-2 (p=0.035) and SDF-1 (p=0.027) predicted for mater benefit in the gemcitabine+placebo group (i.e., worse survival in the gemcitabine+bevacizumab group). Interestingly, when VEGF-D was evaluated using quartile cutpoints, low levels (below Q1, lowest 25% or less than 1092.35 pg/mL VEGF-D) predicted for benefit from bevacizumab (p=0.033) while higher levels (above Q1, top 75% or more than 1092.35 pg/mL VEGF-D) of VEGF-D predicted for lack of benefit from bevacizumab (p=0.035). The data is shown graphically in FIG. 3. Again, low levels of Ang-2 and SDF-1 favored the placebo group, but a non-significant trend was noted for higher levels of these analytes predicting for benefit from bevacizumab, VEGF-D was seen to be predictive across both sides of the Q1 split.

TABLE 12

Univariate Overall Survival Predictive Markers at baseline (EDTAs) for Gem + Bev vs Gem + Placebo

| Analyte | Cutoff | p-value | HR | 95% CI | Gem + Placebo | | Gem + Bev | |
|---|---|---|---|---|---|---|---|---|
| | | | | | Median Survival | 95% CI | Median Survival | 95% CI |
| Ang2 | <median | 0.0346 | 1.4 | (1.02, 1.92) | 9.6 | (8.1, 10.6) | 7.0 | (5.7, 8.7) |
| SDF-1 | <median | 0.0273 | 1.4 | (1.04, 1.94) | 8.4 | (6.3, 9.7) | 5.4 | (4.8, 7.4) |
| SDF-1 | <Q1 | 0.0304 | 1.6 | (1.04, 2.56) | 9.2 | (5.9, 10.7) | 4.9 | (3.3, 7.9) |
| VEGF-D | >Q1 | 0.0346 | 1.3 | (1.04, 1.74) | 6.9 | (5.7, 9.0) | 5.8 | (4.8, 7.1) |
| VEGF-D | <Q1 | 0.0332 | 0.6 | (0.39, 0.96) | 5.4 | (3.6, 9.4) | 6.5 | (5.0, 11.0) |

Figure 4:
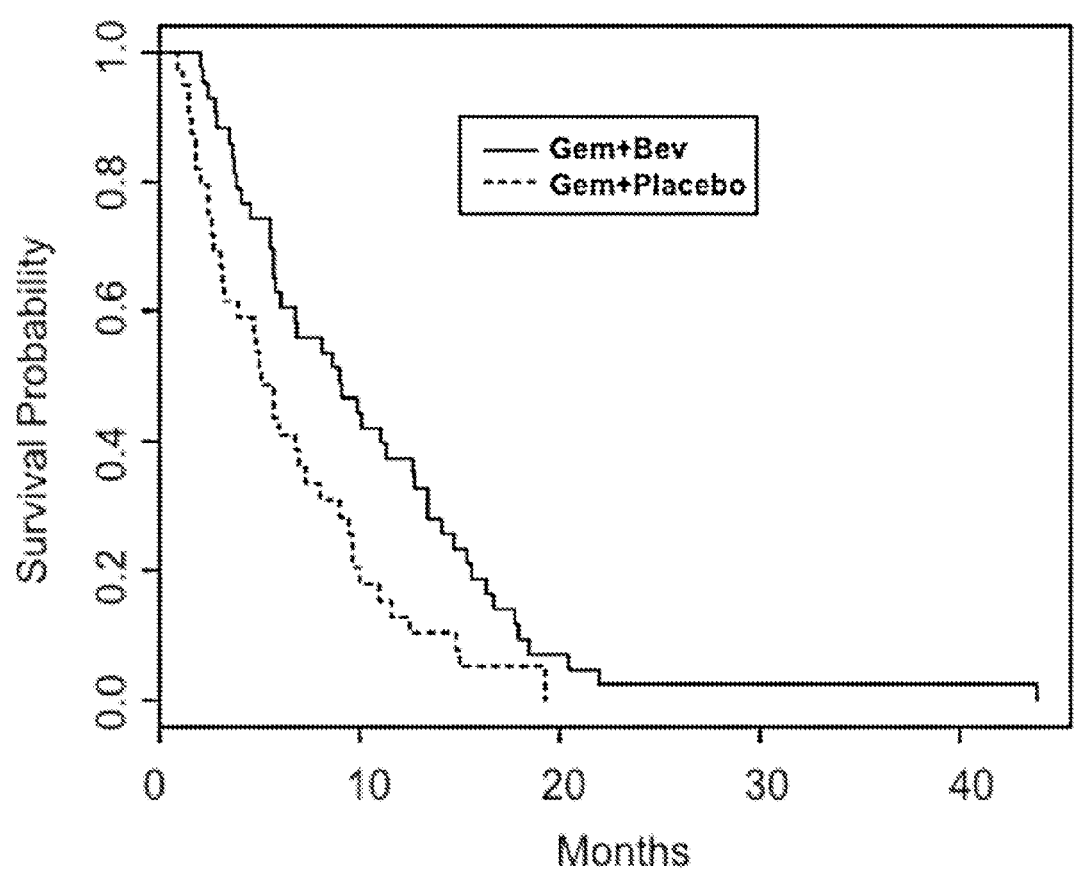
FIG. 4 is a Kaplan-Meier plot showing the survival data of subjects in the gemcitabine+bevacizumab group (solid line) distinguished by high SDF-1 and low OPN as compared to the gemcitabine+placebo group (dashed line).
Figure 5:
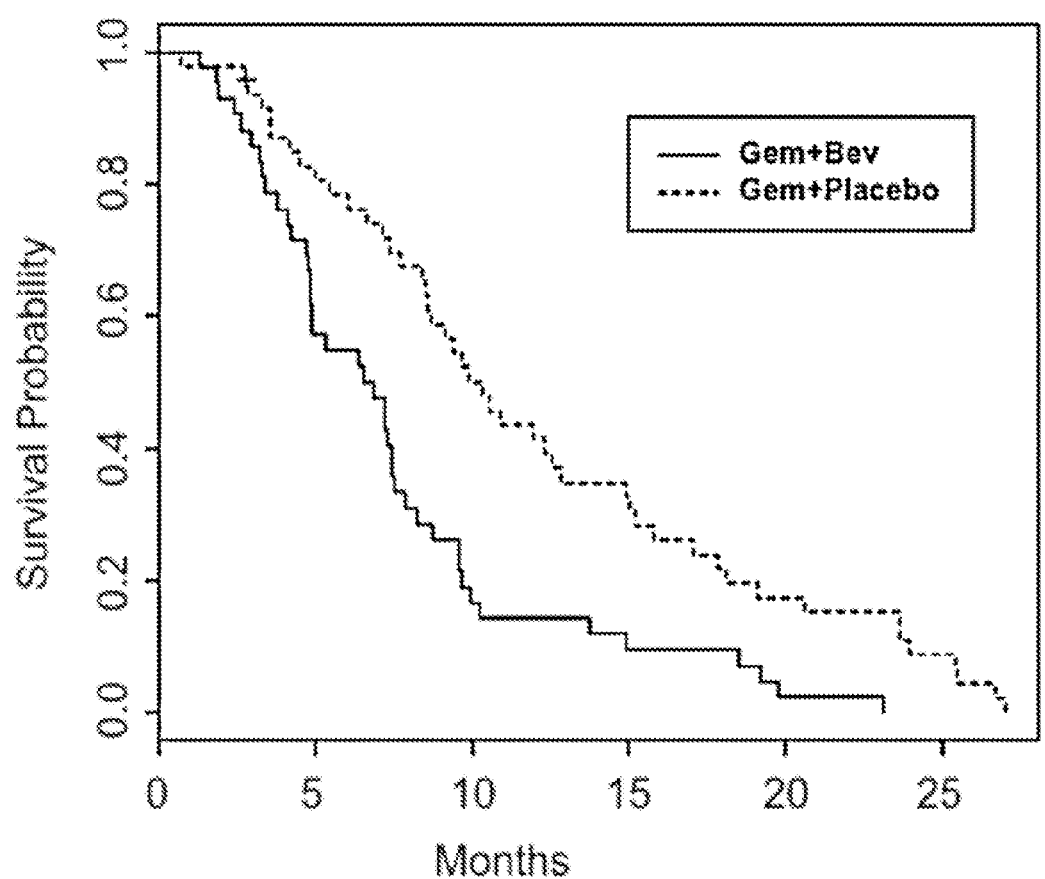
FIG. 5 is a Kaplan-Meier plot showing the survival data of subjects is improved in the gemcitabine+placebo group (dashed lines) with low SDF-1 and low ANG-2 as compared to the gemcitabine+bevacizumab group (solid lines).

Next, the predictive impact of analyte pairs was evaluated. All pairs tested contained a factor that was found to be predictive upon univariate analysis. This bivariate analysis identified 12 pairs of analytes that were statistically significant predictors of benefit or lack of benefit from bevacizumab after correction for multiple testing (Table 13). The bivariate model which most strongly predicted for improved survival in the gemcitabine+bevacizumab group was the combination of SDF-1b (>median) and OPN (<median). See FIG. 4. The model was associated with a hazard ratio of 0.55, with corresponding median survivals of 5.1 and 9.0 months for the gemcitabine+placebo group (shown in dashed lines) and gemcitabine+bevacizumab (shown in solid lines), respectively. Alternatively, the bivariate model which most strongly predicted for worse survival in the gemcitabine+bevacizumab group was found to be SDF1 (<median) and Ang2 (<median). See FIG. 5. This model was associated with a hazard ratio of 2.2, with corresponding median survivals of 10.4 and 6.7 months for the gemcitabine placebo group (shown in dashed lines) and gemcitabine+bevacizumab (shown in solid lines).

xenograft and genetically modified mouse models of pancreatic cancer. Clinical trials with agents that inhibit these pathways are ongoing in various cancers, including pancreatic cancer; however, the value of targeting these factors in patients with pancreatic cancer is not yet known.

Multiple candidate markers of sensitivity and resistance to bevacizumab were also identified. The ability to assess for treatment interactions that can suggest such markers is a key advantage of randomized studies. The predictive importance of VEGF-D was highly statistically significant and low levels were associated with benefit from bevacizumab, and high levels were associated with resistance to bevacizumab, VEGF-D however was not found to be a general prognostic factor in this study. In addition to VEGF-D, low levels of SDF1 and Ang2 were identified on univariate analyses as potential predictors of resistance to bevacizumab. Bivariate analyses confirmed the potential importance of these findings, and suggested that high levels of SDF1 and low levels of OPN may predict for sensitivity to bevacizumab. Interestingly, Ang2 was noted to have significant general prognostic

TABLE 13

Bivariate Overall Survival Predictive Markers at baseline (EDTAs) for Gem + Bev vs Gem + placebo using a median cutoff.

| | | | | | | | Gem + Placebo | | | Gem + Bev | | |
|---|---|---|---|---|---|---|---|---|---|---|---|---|
| Analyte | cutoff | Analyte | cutoff | p-value | HR | 95% CI | N | Median Survival | 95% CI | N | Median Survival | 95% CI |
| SDF-1 | <med | PDGF-AA | >med | 0.0047 | 2.2 | (1.3, 3.7) | 29 (1) | 7.7 | (4.8, 9.1) | 34 (0) | 4.7 | (3.8, 7.2) |
| SDF-1 | <med | IGFBP-3 | >med | 0.0054 | 1.2 | (1.9, 2.9) | 45 (0) | 8.6 | (6.7, 10.6) | 39 (0) | 5.2 | (4.8. 7.5) |
| SDF-1 | <med | VEGF-R1 | >med | 0.0058 | 1.9 | (1.2, 3.2) | 34 (0) | 9.1 | (5.9, 12.4) | 41 (0) | 4.9 | (4.1, 7.2) |
| SDF-1 | <med | MCP-1 | <med | 0.0062 | 1.8 | (1.2, 2.7) | 49 (1) | 9.7 | (8.5, 12.9) | 44 (0) | 5.9 | (4.8, 7.9) |
| SDF-1* | >med | OPN* | <med | 0.0073 | 0.55 | (0.35, 0.85) | 39 (0) | 5.1 | (3.2, 8.1) | 43 (0) | 9.0 | (5.8, 13.4) |
| ANG-2 | <med | SDF-1 | <med | 0.0005 | 2.2 | (1.4, 3.4) | 46 (1) | 10.4 | (8.6, 15.0) | 42 (0) | 6.7 | (4.9, 7.9) |
| ANG-2 | <med | FGFb | <med | 0.0053 | 1.2 | (1.9, 3.1) | 30 (1) | 10.5 | (8.7, 19.1) | 51 (0) | 6.9 | (5.7, 9.5) |
| ANG-2 | <med | OPN | >med | 0.0055 | 2.1 | (1.2, 3.6) | 30 (1) | 8.7 | (6.8, 11.6) | 36 (0) | 5.4 | (4.8, 7.2) |
| ANG-2 | <med | HGF | >med | 0.0070 | 1.9 | (1.2, 3.2) | 35 (2) | 7.4 | (5.6, 9.9) | 36 (0) | 5.1 | (4.2, 6.9) |
| ANG-2 | <med | VCAM-1 | <med | 0.0092 | 1.7 | (1.1, 2.6) | 43 (0) | 10.6 | (9.4, 15.8) | 52 (0) | 7.0 | (5.5, 9.5) |
| HGF | >med | MCP-1 | <med | 0.0007 | 2.5 | (1.5, 4.3) | 34 (1) | 8.0 | (5.9, .9) | 32 (0) | 4.9 | (4.2, 6.5) |
| HGF | >med | IGF-1 | >med | 0.0068 | 2.0 | (1.2, 3.4) | 28 (0) | 8.0 | (6.8, 12.5) | 36 (0) | 5.0 | (4.1, 7.1) |
| VEGF-C | <med | GROα | >med | 0.0081 | 2.2 | (1.2, 4.1) | 21 (0) | 9.1 | (4.7, 14.8) | 34 (0) | 4.8 | (3.2, 7.9) |

This multiplex angiome analysis of CALGB 80303 is one of the largest such analyses reported to date, and the first in metastatic pancreatic cancer. In this large multicenter study, technical analyses were robust with good sensitivity and low variability, which were generally comparable to single kit ELISAs. Unsupervised hierarchical clustering identified potential patterns of analyte expression, with suggested grouping among VEGF/PDGF family members, TGFβ family members, and various inflammatory and coagulation factors. Such analyses, particularly across cancer types and in the settings of tumor response and progression, may provide novel insights into the co and counter regulation of these factors and their underlying biology.

Multiple prognostic markers were identified. This analysis is the largest and most comprehensive to date. These laboratory based prognostic markers were more powerful than traditional clinical factors and they remained highly statistically significant even after adjustment for known clinical factors. Most of these markers are involved in tumor related angiogenesis, inflammation, and coagulation, confirming the clinical importance of the underlying pathophysiology of pancreatic cancer. Indeed, ras mutations, which are present in approximately 90% of pancreatic adenocarcinomas, have been associated with the up-regulation of multiple factors related to inflammation and inflammatory angiogenesis and targeting these factors has been shown to inhibit the growth of importance, while SDF1 was not. Ang2 and SDF1 are known to promote angiogenesis and thus the finding that low levels of these factors are associated with lack of benefit from bevacizumab may appear somewhat counter-intuitive. However, these factors are also associated with active angiogenesis and are known to be regulated by VEGF. Thus the current data are consistent with the known biology of both Ang2 and SDF1 being VEGF context dependent.

In conclusion, multiple factors with strong prognostic impact for patients with pancreatic cancer were identified in the current analysis. In addition, VEGF-D was identified as a strong candidate for predicting sensitivity and resistance to bevacizumab in this population. Other candidates were also identified, highlighting the known complexity of tumor angiogenesis and pancreatic cancer.

We claim:

1. A method of predicting responsiveness of pancreatic cancer in a subject to a cancer therapy including a VEGF targeting agent comprising: obtaining a sample from the subject; measuring an protein expression level of at least one biomarker selected from Ang-2, SDF-1 and VEGF-D in the sample from the subject; and treating the subject with a VEGF targeting agent if the expression level of Ang-2 is greater than 305 pg/mL, the expression level of SDF-1 is more than 1100 pg/mL, or the expression level of VEGF-D is less than 1100 pg/mL.

2. The method of claim 1, wherein the expression level of ANG-2 is measured and further comprising measuring the expression level of at least one of SDF-1, FGFb, OPN, HGF and VCAM-1, and wherein the subject is not treated with the VEGF targeting agent if the expression level of Ang-2 is less than 305 pg/mL and the expression level of SDF-1 is less than 1100 pg/mL, FGFb is less than 30 pg/mL, VCAM-1 is less than 1,700 ng/mL, OPN is more than 73 ng/mL or HGF is more than 800 pg/mL.

3. The method of claim 1, wherein the expression level of SDF-1 is measured and further comprising measuring the expression level of at least one of OPN, PDGF-AA, IGFBP-3, VEGF-R1 or MCP-1, wherein the subject is treated with the VEGF targeting agent if the expression level of SDF-1 is more than 1100 pg/mL and OPN is less than 75 ng/mL, and wherein the subject is not treated with the VEGF targeting agent if the expression level of SDF-1 is less than 1100 pg/mL, and the expression level of MCP-1 is less than 525 pg/mL, PDGF-AA is more than 230 pg/mL, IGFBP-3 is more than 700,000 ng/mL, or VEGF-R1 is more than 120 pg/mL.

4. The method of claim 1, wherein the expression level of Ang-2, SDF-1 and VEGF-D are determined.

5. The method of claim 1, wherein the sample is blood, plasma, serum, or urine.

6. The method of claim 1, wherein the protein expression level is determined by a method selected from ELISA, immunofluorescence, FACS analysis, Western blot, magnetic immunoassays, and antibody-based microarrays.

* * * * *